US006797842B2

(12) United States Patent
Ishii et al.

(10) Patent No.: US 6,797,842 B2
(45) Date of Patent: Sep. 28, 2004

(54) PROCESS FOR PRODUCING OPTICALLY ACTIVE 1-(FLUORO- OR TRIFLUOROMETHYL-SUBSTITUTED PHENYL) ETHYLAMINE AND PROCESS FOR PURIFYING SAME

(75) Inventors: Akihiro Ishii, Saitama (JP); Manabu Yasumoto, Saitama (JP); Yokusu Kuriyama, Saitama (JP); Masatomi Kanai, Saitama (JP); Takashi Hayami, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/853,085

(22) Filed: May 11, 2001

(65) Prior Publication Data

US 2002/0103400 A1 Aug. 1, 2002

(30) Foreign Application Priority Data

| May 11, 2000 | (JP) | ................................. | 2000-138349 |
| May 15, 2000 | (JP) | ................................. | 2000-142460 |
| Jun. 20, 2000 | (JP) | ................................. | 2000-185405 |
| Dec. 4, 2000 | (JP) | ................................. | 2000-369007 |
| Dec. 20, 2000 | (JP) | ................................. | 2000-387724 |
| Feb. 28, 2001 | (JP) | ................................. | 2001-054716 |
| Apr. 9, 2001 | (JP) | ................................. | 2001-109735 |

(51) Int. Cl.$^7$ ...................... C07C 211/00; C07C 209/00
(52) U.S. Cl. ...................................... 564/384; 564/385
(58) Field of Search ................................. 564/384, 385, 564/388

(56) References Cited

U.S. PATENT DOCUMENTS 6,211,244 B1 * 4/2001 Van Wagenen et al.

FOREIGN PATENT DOCUMENTS

| DE | 3819438 | 1/1989 |
| JP | 9278718 | 10/1997 |
| JP | 09278718 | * 10/1997 |

OTHER PUBLICATIONS

Siemeon T. Pickard, et al., "Optically Active Amines. 34.[1] Application of the Benzene Chirality Rule to Ring–Substituted Phenylcarbinamines and Carbinols" J.Am.Chem.Soc. 1990.

Shinichi Itsuno, "Asymmetric Synthesis Using Chirally Modified Borohydrides. Part 3. Enantioselective Reduction of Ketones and Oxime Ethers with Reagents Prepared from Borane and Chiral Amino Alcohols" J.Chem.Soc. 1985.

Howard E. Smith, et al. "Optically Active Amines. 31. Spectral Observations on the Substituted Benzene Chromphore" J.Am.Chem.Soc. 1983.

Yutaka Ie, "A new benchmark for the non–enzymatic enantioselective acylation of amines: use of a planar–chiral derivative of 4–pyrrolidinopyridine as the acylating agent" Chem.Communication 2000.

Kazushi Kinbara, "Effect of a Substituent on an Aromatic Group in Diastereomeric Resolution" Tetrahedron, 2000.

Kazushi Kinbara, "A high–performance, tailor–made resolving agent: remarkable enhancement of resolution ability by introducing a naphthyl group into the fundamental skeleton" The Royal Society of Chemistry, 2000.

Shunsuke Takenaka, "Induced Circular Dichroism of Chiral Amine–Benzoylbenzoic Acid Systems" J. Am.Chem. .Soc.1978.

G. Bringmann, "A Facile–Method for the Asymmetric Synthesis of Enantiomerically Pure 1–(2–Fluorophenyl)–Ethylamine" J.Fluorine Chemistry 1990.

G. Bringmann, "Enantiomerically Pure Oxygenated 1–Phenylethylamines from Substituted Acetophenones: By Reductive Amination and Regiospecific Benzylic Cleavage" Tetrahedron 1989.

* cited by examiner

Primary Examiner—Johann Richter
Assistant Examiner—Paul A. Zucker
(74) Attorney, Agent, or Firm—Crowell & Moring LLP

(57) ABSTRACT

An optically active 1-(fluoro- or trifluoromethyl-substituted phenyl)ethylamine is produced with high optical purity and in an industrially simple and efficient manner by asymmetrically reducing an optically active imine, obtained by dehydration and condensation of a fluoro- or trifluoromethyl-substituted phenylmethyl ketone and an optically active primary amine under acidic conditions, using a hydride reducing agent to convert to an optically active secondary amine, and subjecting the secondary amine or its salt of an inorganic acid or organic acid to hydrogenolysis. In addition, an optically active 1-(fluoro- or trifluoromethyl-substituted phenyl)ethylamine is purified to an even higher optical purity in an industrially simple and efficient manner by converting the optically active secondary amine of the synthetic intermediate obtained by asymmetric reduction, or an optically active 1-(3,5-bis-trifluoromethylphenyl) ethylamine, one of the target compounds, to an inorganic or organic acid salt followed by recrystallization purification. This ethylamine is an important intermediate of pharmaceuticals and agricultural chemicals.

34 Claims, No Drawings

PROCESS FOR PRODUCING OPTICALLY ACTIVE 1-(FLUORO- OR TRIFLUOROMETHYL-SUBSTITUTED PHENYL) ETHYLAMINE AND PROCESS FOR PURIFYING SAME

BACKGROUND OF THE INVENTION

The present invention relates to a production process and purification process of optically active 1-(fluoro- or trifluoromethyl-substituted phenyl)ethylamine that is an important intermediate of pharmaceuticals and agricultural chemicals.

Optically active 1-(fluoro- or trifluoromethyl-substituted phenyl)ethylamine is an important intermediate of pharmaceuticals and agricultural chemicals. The following technologies have been reported as production processes and purification processes of the optically active amine.

For example, although a production process of optically active 1-(3,5-bis-trifluoromethylphenyl)ethylamine, which is a compound in which two trifluoromethyl groups have been substituted, was reported in J. Am. Chem. Soc., 112, 5741 (1990), and was synthesized with reference to asymmetric reduction of oxime derivative described in J. Chem. Soc., Perkin Trans. 1, 2039 (1985), its chemical yield and optical purity were low at 15% and 71% ee(S), respectively.

In addition, a production process of optically active 1-(2-trifluoromethylphenyl)ethylamine (ortho-trifluoromethyl form), which is a compound in which one trifluoromethyl group has been substituted, was also reported in the above reference, and although it was synthesized by a similar procedure, its chemical yield and optical purity were low at 16% and 76% ee(S), respectively.

A production process of optically active 1-(3-trifluoromethylphenyl)ethylamine (meta-trifluoromethyl form) was reported in Japanese Unexamined Patent Publication No. 9-278718, and although optical resolution was carried out by 1-mandelic acid, the chemical yield and optical purity of the precipitated diastereomer salt crystals were low at 45% and 60% ee (S), respectively (the chemical yield and optical purity of the mother liquor and crystal washings were 55% and 50% ee (R), respectively). In addition, although it is also synthesized by a technique similar to the case of the ortho-trifluoromethyl form, the chemical yield and optical purity were low at 19% and 87% ee (S), respectively (J. Am. Chem. Soc., 112, 5741 (1990)).

A production process of optically active 1-(4-trifluoromethylphenyl)ethylamine (para-trifluoromethyl form) was reported in J. Am. Chem. Soc., 105, 1578 (1983), and although three times of recrystallization were carried out on crystals of a precipitated diastereomer salt in optical resolution by 1-N-acetylleucine, its chemical yield and optical purity were low at 19% and 60% ee(S), respectively. In addition, although this has also been synthesized according to a non-enzymatic enantioselective acylation reaction using a planar-chiral derivative of 4-pyrrolidinopyridine, and it has been reported that the non-reacted S form is concentrated by use of (−)-Ph-PPY*, its chemical yield and optical purity were not described (Chem. Commun., 2000, 119).

A production process of optically active 1-(4-fluorophenyl)ethylamine (para-fluoro form) is reported in Tetrahedron, 56, 6651 (2000), J. Chem. Soc., Perkin Trans. 2, 1339 (2000) and J. Chem. Soc., Perkin Trans. 2, 95 (1978), and although optical resolution was carried out by (S)-3′,4′-methylenedioxymandelic acid, (S)-2-naphthylglycolic acid and (+)-tartaric acid, respectively, in these processes, special resolving agents are required and the resolution efficiency was not always high.

As has been described above, it has not been possible in the prior art to produce optically active 1-(fluoro- or trifluoromethyl-substituted phenyl)ethylamine both efficiently and with high optical purity.

In addition, as the technical background of the present invention, there are provided asymmetric reduction of optically active N-(alkylbenzylidene)-α-methylbenzylamines and their following hydrogenolysis.

To begin with, a description is provided of the former, asymmetric reduction. Although a comparatively large amount of research has been conducted on this type of diastereofacial selective 1,3-asymmetric reduction, examples of asymmetric reduction of optically active imine represented by the general formula [3], which is the target of the present invention, have not been reported, and in the case of asymmetric reduction using hydride reducing agents, since the effects of substitution position of the fluorine atom or trifluoromethyl group along with the number of substituted groups (n) on diastereofacial selectivity cannot be predicted at all, whether or not this is efficient as an industrial production process of the ant corresponding optically active 1-(fluoro- or trifluoromethyl-substituted phenyl) ethylamine has remained unknown.

As an example of a related technology, although an example of carrying out asymmetric reduction of an optically active imine of ortho position, in which R in the general formula [3] is a fluorine atom and n is 1, in a hydrogen atmosphere using a Raney nickel catalyst is reported in J. Fluorine Chem., 49, 67 (1990), the diastereofacial selectivity was extremely low at 37% de, and was not considered to be an efficient industrial production process.

Next, a description is provided of the latter hydrogenolysis. As is represented by the general formula [9]:

[Chemical 13]

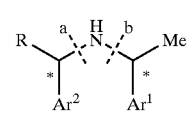

[9]

(wherein, R represents an alkyl group, $Ar^1$ and $Ar^2$ represent aryl groups, and the asterisks (*) represent chiral carbon atoms), the product obtained by the above-mentioned asymmetric reduction has two similar α-alkylaralkyl groups with respect to the nitrogen atom, and in the case of hydrogenolysis, which is a typical process for removing chiral auxiliary group, since only the chiral auxiliary group side (b) cannot be selectively cleaved, it was difficult to employ these series of technologies as a process for asymmetric synthesis of typical optically active α-alkylbenzylamines.

In particular, since the optically active secondary amine represented by the general formula [4], which is a target of the present invention, has methyl groups for both of the alkyl groups, the steric bulkiness at the cleaved sites is nearly the same. In such cases, cleavage must be performed selectively by using the steric or electronic effects of the substitution groups on the aryl groups.

For example, it is reported in DE3819438 and Tetrahedron Lett., 30, 317 (1989) that, in the case of $Ar^2$ having a plurality of electron donating groups such as methoxy groups (R is a methyl group, $Ar^1$ is a phenyl group and the stereochemistry is S—S in the above general formula [9]), cleavage occurs with complete positional selectivity at the chiral auxiliary group side (b) (selectivity (a:b) at the cleavage position is 0:100).

In addition, the case of $Ar^2$ having an electron withdrawing group of chlorine or fluorine at position 2 (ortho position) (R is a methyl group, $Ar^1$ is a phenyl group and the stereochemistry is S—S in the above general formula [9]) is also reported in the above patent (DE3819438) and J. Fluorine Chem., 49, 67(1990), and in this case as well, cleavage is reported to occur selectively at the chiral auxiliary group side (b).

However, under conditions in which the 2-fluoro form (ortho-fluoro form) is subjected to hydrogenolysis by ammonium formate in the presence of a palladium/active carbon catalyst, the selectivity (a:b) at the cleavage position decreases to 11:89 as compared with the above case of $Ar^2$ having electron donating groups, and in order to obtain the target optically active 1-(2-fluorophenyl)ethylamine with a high chemical purity, it was necessary to separate the (S)-α-methylbenzylamine produced as a by-product by column chromatography, thereby preventing this from being an efficient industrial production process. In addition, although examples of the hydrogenolysis carried out in a hydrogen atmosphere in the presence of palladium/active carbon catalyst have also been indicated, since the amount of palladium metal used under the disclosed reaction conditions is extremely high at 2 wt %, and since the hydrogen pressure is also extremely high at 180 bar, these were not considered to be reaction conditions that can be used as an industrial production process.

Hydrogenolysis of optically active secondary amine represented by the general formula [4], which is the target of the present invention, has yet to be reported, the effects of substitution position of the fluorine atom or trifluoromethyl group along with number of substituted groups (n) on the selectivity (a:b) at the cleavage position cannot be predicted, and whether or not it is possible to efficiently convert to the corresponding optically active 1-(fluoro- or trifluoromethyl-substituted phenyl)ethylamine under reaction conditions that can be employed as an industrial production process has been unknown. In other words, even though position 2 (ortho position) is the closest to the cleavage position and is the substitution position that most easily imparts steric or electronic effects, under hydrogenolysis conditions that can be employed as an industrial production process, the selectivity (a:b) at the cleavage position is low, and when this is taken into consideration, as the substitution position of the fluorine atom or trifluoromethyl group moves away from the cleavage position, that selectivity is predicted to further decrease, and among the optically active secondary amines represented by the general formula [4] that are the target of the present invention in particular, in those position 3 (meta position) or position 4 (para position) compounds in which a is 1, hardly any selectivity (a:b) at the cleavage position can be expected, and it was unknown as to whether or not this was efficient as an industrial production process of the corresponding optically active 1-(fluoro- or trifluoromethyl-substituted phenyl)ethylamine.

As has been explained above, in the prior art, it was not possible to obtain optically active 1-(fluoro- or trifluoromethyl-substituted phenyl)ethylamine with high optical purity, industrially easily and efficiently.

SUMMARY OF THE INVENTION

The object of the present invention is to provide an industrially simple and efficient production process and purification process for obtaining an optically active 1-(fluoro- or trifluoromethyl-substituted phenyl)ethylamine having high optical purity.

As a result of earnest studies to solve the above problems, the present inventors showed that by dehydrating and condensing fluoro- or trifluoromethyl-substituted phenylmethyl ketone and optically active primary amine under acidic conditions, by asymmetrically reducing the resulting optically active imine using a hydride reducing agent, and particularly sodium borohydride, converting to an optically active secondary amine with a high degree of diastereofacial selectivity, and by subjecting the secondary amine, its inorganic salt or its organic salt to hydrogenolysis while heating, the amount of metal catalyst used and hydrogen pressure can be significantly reduced and the reaction proceeds with complete selectivity at the cleavage position. More specifically, by conducting hydrogenolysis while heating at 40° C. or higher using a group VIII metal catalyst, and particularly a palladium catalyst, at 0.5 wt % or less when converted as metal in a hydrogen atmosphere of 2 MPa or lower, it was found that optically active 1-(fluoro- or trifluoromethyl-substituted phenyl)ethylamine can be produced in an industrially simple and efficient manner at high optical purity.

In addition, it was found that by converting the optically active secondary amine of the synthetic intermediate obtained by asymmetric reduction, or optically active 1-(3, 5-bis-trifluoromethylphenyl)ethylamine, which is one of the target compounds, to the salt of an inorganic acid or organic acid, and particularly hydrochloric acid, hydrobromic acid, phthalic acid, benzenesulfonic acid, p-toluenesulfonic acid, optically active mandelic acid or optically active tartaric acid, followed by purification by recrystallization, optically active 1-(fluoro- or trifluoromethyl-substituted phenyl) ethylamine can be purified in an industrially simple and efficient manner to an even higher optical purity, thereby leading to completion of the present invention.

The process of the present invention is represented by the following Scheme 1.

Scheme 1

[Chemical 14]

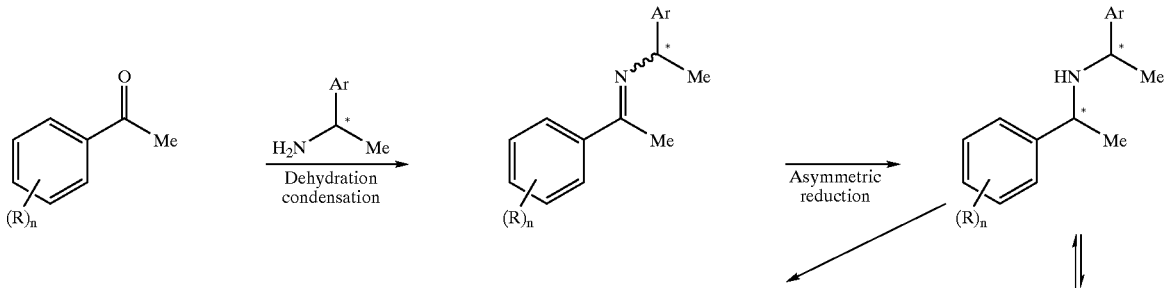

Purification by salt ⇌ (Case of 3,5-bis-trifluoromethyl) 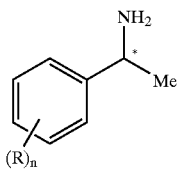 ← Hydrogenolysis — Purification by salt Namely, the present invention is a process for producing an optically active 1-(fluoro- or trifluoromethyl-substituted phenyl)ethylamine represented by the general formula [5]:

[Chemical 17]

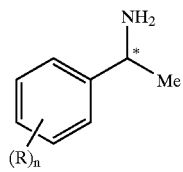 [5]

(wherein, R represents a fluorine atom or trifluoromethyl group, n represents 1 to 5, and it takes an arbitrary substitution position, except for the ortho position when R is a fluorine atom and n is 1, and the asterisk (*) represents a chiral carbon) by asymmetrically reducing an optically active imine represented by the general formula [3]:

[Chemical 15]

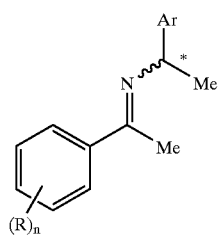 [3]

(wherein, R represents a fluorine atom or trifluoromethyl group, n represents 1 to 5, and it takes an arbitrary substitution position, except for the ortho position when R is a fluorine atom and n is 1, Ar represents a phenyl group or 1- or 2-naphthyl group, and the asterisk (*) represents a chiral carbon) using a hydride reducing agent, converting to an optically active secondary amine represented by the general formula [4]:

[Chemical 16]

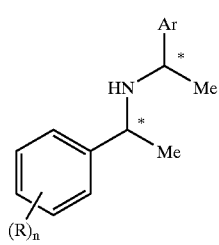 [4]

(wherein, R represents a fluorine atom or trifluoromethyl group, n represents 1 to 5, and it takes an arbitrary substitution position, except for the ortho position when R is a fluorine atom and n is 1, Ar represents a phenyl group or 1- or 2-naphthyl group, and the asterisks (*) represent chiral carbons), and subjecting the secondary amine, its salt of an inorganic acid or its salt of an organic acid to hydrogenolysis.

In addition, the present invention is a purification process characterized in that an optically active secondary amine represented by the general formula [4]:

[Chemical 20]

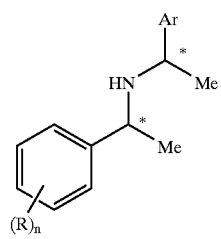 [4]

(wherein, R represents a fluorine atom or trifluoromethyl group, n represents 1 to 5, and it takes an arbitrary substitution position, except for the ortho position when R is a fluorine atom and n is 1, Ar represents a phenyl group or 1- or 2-naphthyl group, and the asterisks (*) represent chiral carbons) is converted to a salt of an inorganic acid or organic acid, followed by purification by recrystallization.

In addition, the present invention is a purification process characterized in that an optically active 1-(3,5-bis-trifluoromethylphenyl)ethylamine represented by the formula [6]:

[Chemical 21]

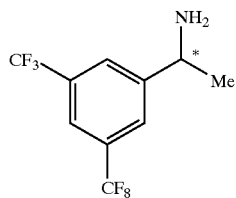

[6]

(wherein, the asterisk (*) represents a chiral carbon) is converted to the salt of an inorganic acid or organic acid followed by purification by recrystallization.

In addition, the present invention is an optically active imine represented by the general formula [7]:

[Chemical 22]

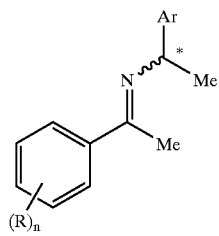

[7]

(wherein, R represents a fluorine atom or trifluoromethyl group, n represents 1 to 5, and it takes an arbitrary substitution position, except for the ortho position and the para position when R is a fluorine atom and n is 1, Ar represents a phenyl group or 1- or 2-naphthyl group, and the asterisk (*) represents a chiral carbon).

In addition, the present invention is an optically active secondary amine represented by the general formula [4]:

[Chemical 23]

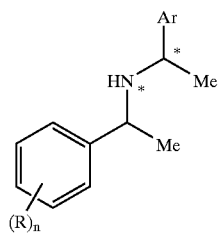

[4]

(wherein, R represents a fluorine atom or trifluoromethyl group, n represents 1 to 5, and it takes an arbitrary substitution position, except for the ortho position when R is a fluorine atom and n is 1, Ar represents a phenyl group or 1- or 2-naphthyl group, and the asterisks (*) represent chiral carbons).

In addition, the present invention is an optically active 1-(fluoro-substituted phenyl)ethylamine represented by the general formula [8].

[Chemical 24]

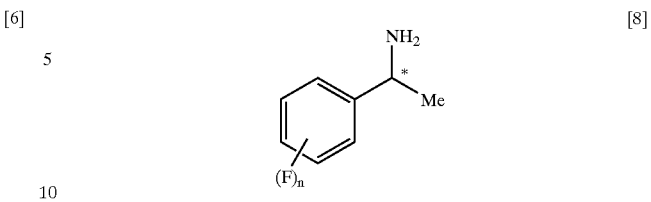

[8]

(wherein, n represents 1 to 5, and it takes an arbitrary substitution position, except for the ortho position and the para position when n is 1, and the asterisk (*) represents a chiral carbon).

In addition, the present invention is a salt of an inorganic acid or organic acid of an optically active secondary amine represented by the general formula [4]:

[Chemical 25]

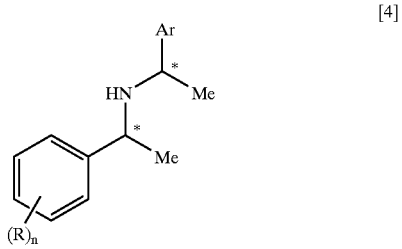

[4]

(wherein, R represents a fluorine atom or trifluoromethyl group, n represents 1 to 5, and it takes an arbitrary substitution position, except for the ortho position when R is a fluorine atom and n is 1, Ar represents a phenyl group or 1- or 2-naphthyl group, and the asterisks (*) represent chiral carbons).

In addition, the present invention is a salt of an inorganic acid or organic acid of an optically active 1-(3,5-bis-trifluoromethylphenyl)ethylamine represented by the formula [6]:

[Chemical 26]

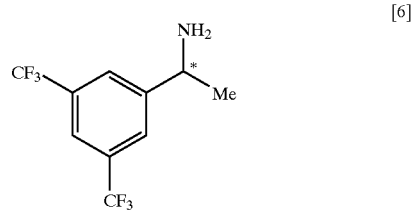

[6]

(wherein, the asterisk represents a chiral carbon).

In addition, the present invention is the above salt wherein the organic acid comprises p-toluenesulfonic acid, optically active mandelic acid or optically active tartaric acid.

DESCRIPTION OF THE PREFERRED EMBODIMENTS

The following provides a detailed explanation of the production process and purification process of an optically active 1-(fluoro- or trifluoromethyl-substituted phenyl) ethylamine of the present invention.

According to the present invention, an optically active 1-(fluoro- or trifluoromethyl-substituted phenyl)ethylamine, which is an important intermediate of pharmaceuticals and agricultural chemicals, can be obtained in an industrially simple and efficient manner with high optical purity.

The production process of the present invention comprises three steps consisting of a step in which an optically active imine is produced by dehydration and condensation of a fluoro- or trifluoromethyl-substituted phenylmethyl ketone and an optically active primary amine under acidic conditions (Step 1), a step in which an optically active secondary amine is produced by asymmetrically reducing the imine using a hydride reducing agent (Step 2), and a step in which an optically active 1-(fluoro- or trifluoromethyl-substituted phenyl)ethylamine is produced by subjecting the secondary amine or its salt of an inorganic acid or organic acid to hydrogenolysis (Step 3).

In Step 1 of the present invention, an optically active imine represented by the general formula [3] can be produced in an industrially efficient manner by the following method.

Namely, it can be produced by subjecting the fluoro- or trifluoromethyl-substituted phenylmethyl ketone represented by the general formula [1] and the optically active primary amine represented by the general formula [2] to dehydration and condensation under acidic conditions.

As the fluoro- or trifluoromethyl-substituted phenylmethyl ketone represented by the general formula [1], there are cited 3-fluorophenylmethyl ketone, 4-fluorophenylmethyl ketone, 2,3-difluorophenylmethyl ketone, 2,4-difluorophenylmethyl ketone, 2,5-difluorophenylmethyl ketone, 2,6-difluorophenylmethyl ketone, 3,4-difluorophenylmethyl ketone, 3,5-difluorophenylmethyl ketone, 2,3,4-trifluorophenylmethyl ketone, 3,4,5-trifluorophenylmethyl ketone 2,4,5-trifluorophenylmethyl ketone, 2,3,5-trifluorophenylmethyl ketone, 2,3,6-trifluorophenylmethyl ketone, 2,4,6-trifluorophenylmethyl ketone, 2,3,5,6-tetrafluorophenylmethyl ketone, 2,4,5,6-tetrafluorophenylmethyl ketone, 3,4,5,6-tetrafluorophenylmethyl ketone, 2,3,4,5,6-pentafluorophenylmethyl ketone, 2-trifluoromethylphenylmethyl ketone, 3-trifluoromethylphenylmethyl ketone, 4-trifluoromethylphenylmethyl ketone, 2,3-bis-trifluoromethylphenylmethyl ketone, 2,4-bis-trifluoromethylphenylmethyl ketone, 2,5-bis-trifluoromethylphenylmethyl ketone, 2,6-bis-trifluoromethylphenylmethyl ketone, 3,4-bis-trifiaoromethylphenylmethyl ketone, 3,5-bis-trifluoromethylphenylmethyl ketone, 2,3,4-tris-trifluoromethylphenyl methyl ketone, 3,4,5-tris-trifluoromethylphenylmethyl ketone, 2,4,5-tris-trifluoromethylphenylmethyl ketone, 2,3,5-tris-trifluoromethylphenylmethyl ketone, 2,3,6-tris-trifluoromethylphenylmethyl ketone, 2,4,6-tris-trifluoromethylphenylmethyl ketone, 2,3,5,6-tetrakis-trifluoromethylphenylmethyl ketone, 2,4,5,6-tetrakis-trifluoromethylphenylmethyl ketone and 3,4,5,6-tetrakis-trifluoromethylphenylmethyl ketone.

As the optically active primary amine represented by the general formula [2], 1-phenylethylamine, 1-1'-naphthylethylamine and 1-2'-naphthylethylamine are cited. Among these, 1-phenylethylamine and 1-2'-naphthylethylamine are preferable, while 1-phenylethylamine is particularly preferable. In addition, since the primary amine is present in the R form or S form, the optically active imine represented by the general formula [3] that is derived therefrom is also present in the R form or S form. However, these enantiomers should be suitably used according to the absolute configuration of the target product.

The amount for use of the optically active primary amine represented by the general formula [2] should normally be 1 molar equivalent or more, preferably 1–10 molar equivalents, and particularly preferably 1–5 molar equivalents, relative to the fluoro- or trifluoromethyl-substituted phenylmethyl ketone represented by the general formula [1].

Since the present reaction is a dehydration and condensation between the fluoro- or trifluoromethyl-substituted phenylmethyl ketone represented by the general formula [1] and the optically active primary amine represented by the general formula [2], the reaction is carried out while removing the water formed as a by-product under acidic conditions. Preferably, water formed as a by-product is removed with a Dean-Stark tube under refluxing conditions using a solvent that is immiscible with water, that has a specific gravity less than water and that is azeotropic with water.

As the reaction solvent, aromatic hydrocarbon solvents such as benzene, toluene, ethylbenzene, xylene and mesitylene are preferable, and toluene is particularly more preferable. These reaction solvents can either be used alone or in combination.

Although the amount of reaction solvent used is required to be an amount that is capable of azeotropically removing the amount of water theoretically formed as a by-product, the amount used can be reduced dramatically by using a Dean-Stark tube.

As the acid catalyst, there are cited organic acids such as benzenesulfonic acid, p-toluenesulfonic acid and 10-camphorsulfonic acid, and inorganic acids such as hydrochloric acid, sulfuric acid, phosphoric acid, zin chloride and titanium tetrachloride. Among these, p-toluenesulfonic acid, sulfuric acid and zinc chloride are preferable, while p-toluenesulfonic acid and zinc chloride are particularly more preferable.

The amount of acid catalyst used should be used in catalytic amount, preferably 0.001–0.9 molar equivalents, and particularly preferably 0.005–0.5 molar equivalents, relative to the fluoro- or trifluoromethyl-substituted phenylmethyl ketone represented by the general formula [1].

Temperature conditions are such that the temperature can be within a range from the azeotropic temperature of the solvent used and water to the boiling point of the solvent, and is preferably close to the boiling point of the solvent used in particular.

In the after-treatment of Step 1, following completion of the reaction, a crude product can be obtained by carrying out a normal after-treatment procedure. The crude product is subjected to a purification procedure such as active carbon, distillation, recrystallization or column chromatography as necessary to allow obtaining of the target optically active imine represented by the general formula [3] at high chemical purity.

In addition, in Step 2 of the present invention, the optically active secondary amine represented by the general formula [4] can be produced in an industrially efficient manner by the method described below.

Namely, it can be produced by asymmetrically reducing the optically active imine represented by the general formula [3] produced in Step 1 using a hydride reducing agent.

As the hydride reducing agent, there are cited aluminum hydrides such as (i-Bu)$_2$AlH, (i-Bu)$_3$Al, [2,6-(t-Bu)$_2$-4-MePh]Al(i-Bu)$_2$, LiAlH$_4$, LiAlH(OMe)$_3$, LiAlH(O-t-Bu)$_3$ and NaAlH$_2$(OCH$_2$CH$_2$OCH$_3$)$_2$; boron hydrides such as diborane, BH$_3$.THF, BH$_3$.SMe$_2$, BH$_3$.NMe$_3$, 9-BBN, NaBH$_4$, NaBH$_4$—CeCl$_3$, LiBH$_4$, Zn(BH$_4$)$_2$, Ca(BH$_4$)$_2$, LinBuBH$_3$, NaBH(OMe)$_3$, NaBH(OAc)$_3$, NaBH$_3$CN, Et$_4$NBH$_4$, Me$_4$NBH(OAc)$_3$, (n-Bu)$_4$NBH$_3$CH, (n-Bu)$_4$NBH(OAc)$_3$, Li(s-Bu)$_3$BH, K(s-Bu)$_3$BH, LiSia$_3$BH, KSia$_3$BH, LiEt$_3$BH, KPh$_3$BH, (Ph$_3$P)$_2$CuBH$_4$, ThxBH$_2$, Sia$_2$BH, catechol borane, IpcBH$_2$ and Ipc$_2$BH; and silicon hydrides such as Et$_3$SiH, PhMe$_2$SiH, Ph$_2$SiH$_2$ and PhSiH$_3$—Mo(CO)$_6$. Among these, LiAlH$_4$, diborane, NaBH$_4$ and LiBH$_4$ are preferable, while NaBH$_4$ is particularly more preferable. These hydride reducing agents can also be used in the presence of various inorganic salts.

The amount of hydride reducing agent used should normally be 0.25 molar equivalents or more, preferably 0.25–10 molar equivalents, and particularly preferably 0.25–7 molar equivalents, relative to the optically active imine represented by the general formula [3].

As the reaction solvent, there are cited aliphatic hydrocarbons such as n-pentane, n-hexane, c-hexane and n-heptane; aromatic hydrocarbons such as benzene, toluene, xylene and mesitylene; halogenated hydrocarbons such as methylene chloride, chloroform and 1, 2-dichloroethane; ethers such as diethyl ether, tetrahydrofuran, t-butylmethyl ether and dioxane; esters such as ethyl acetate and n-butyl acetate; nitriles such as acetonitrile and propionitrile; alcohols such as methanol, ethanol, n-propanol and i-propanol; and carboxylic acids such as acetic acid, propionic acid and butyric acid. Among these, diethyl ether, tetrahydrofuran, t-butylmethyl ether, methanol, ethanol and i-propanol are preferable, while tetrahydrofuran, methanol, ethanol and i-propanol are particularly more preferable. These reaction solvents can be used either alone or in combination.

The temperature condition is from −100 to 100° C., preferably from −80 to 80° C., and particularly more preferably from −60 to 60° C.

In the after-treatment of Step 2, following completion of the reaction, a crude product can be obtained by carrying out a normal after-treatment procedure. The crude product is subjected to a purification procedure such as active carbon, distillation, recrystallization or column chromatography as necessary to allow obtaining of the target optically active secondary amine represented by the general formula [4] at high chemical purity.

In addition, an optically active 1-(fluoro- or trifluoromethyl-substituted phenyl)ethylamine can be obtained at even higher optical purity by converting the optically active secondary amine represented by the general formula [4] to the salt of an inorganic acid or organic acid followed by purification by recrystallization at this stage. The purification will be described hereinafter.

In addition, in step 3 of the present invention, an optically active 1-(fluoro- or trifluoromethyl-substituted phenyl)ethylamine represented by the general formula [5] can be produced in an industrially efficient manner by the method described below.

Namely, it can be produced by subjecting the optically active secondary amine represented by the general formula [4] that was produced in Step 2, or its salt of an inorganic acid or organic acid to hydrogenolysis, using a metal catalyst of group VIII at 0.5 wt % or less when converted as metal while heating at 40° C. or higher in a hydrogen atmosphere of 2 MPa or less.

As group VIII metal catalyst, there are cited platinum catalysts such as platinum oxide, platinum/active carbon and platinum black; nickel catalysts such as reduced nickel, Raney nickel and platinum-Raney nickel; cobalt catalysts such as Raney cobalt; ruthenium catalysts such as ruthenium oxide and ruthenium/active carbon; rhodium catalysts such as rhodium/active carbon, rhodium/alumina and rhodium-platinum oxide; iridium catalysts such as iridium black; and palladium catalysts such as palladium/active carbon, palladium hydroxide, palladium black, palladium/barium sulfate, palladium/strontium carbonate, palladium/calcium carbonate, palladium/calcium carbonate-lead diacetate, palladium/barium sulfate-quinoline, palladium/alumina, palladium sponge, palladium chloride, palladium acetate, palladium acetylacetonate, bis(dibenzylideneacetone) palladium, tetrakis(triphenylphosphine)palladium, dichloro [bis(triphenylphosphine)]palladium, dichloro[bis (diphenylphosphino)methane]palladium, dichloro[bis (diphenylphosphino)ethane]palladium, dichloro[1,3-bis (diphenylphosphino)propane]palladium, dichloro[1,4-bis (diphenylphosphino)butane]palladium, dichloro(1,5-cyclooctadiene)palladium, dichloro[bis(benzonitrile)] palladium, dichloro[bis(acetonitrile)]palladium and [bis (triphenylphosphine)]palladium acetate. Among these, platinum catalysts, rhodium catalysts and palladium catalysts are preferable, and platinum/active carbon, rhodium/ active carbon and palladium/active carbon are particularly more preferable. These group VIII metal catalysts can be used alone or in combination. In the case of using a catalyst in which a metal is loaded onto a support, that loaded amount is 0.1–50 wt %, preferably 0.5–30 wt %, and particularly more preferably 1–20 wt %. In addition, in order to enhance safety during handling or to prevent oxidation of the metal surface, a combination with water, mineral oil or the like can be used.

The amount of group VIII metal catalyst used is normally 0.5 wt % or less, preferably 0.001–0.4 wt %, and particularly more preferably 0.005–0.3 wt %, when converted as metal relative to the optically active secondary amine represented by the general formula [4], or its salt of an inorganic acid or organic acid.

Although the amount of hydrogen used should normally be equal to or greater than 1 molar equivalent relative to the optically active secondary amine represented by the general formula [4] or its salt of an inorganic acid or organic acid, it is normally used in excess since the reaction is carried out in a hydrogen, atmosphere.

The hydrogen pressure is 2 MPa or less, preferably 0.01–1.5 MPa, and particularly more preferably 0.05–1 MPa.

As the reaction solvent, there are cited aliphatic hydrocarbons such as n-pentane, n-hexane, c-hexane and n-heptane; aromatic hydrocarbons such as benzene, toluene. xylene and mesitylene; ethers such as diethyl ether, tetrahydrofuran, t-butylmethyl ether and dioxane; esters such as ethyl acetate and n-butyl acetate; alcohols such as methanol, ethanol, n-propanol and i-propanol; carboxylic acids such as acetic acid, propionic acid and butyric acid; acidic aqueous solutions such as hydrochloric acid, sulfuric acid, hydrobromic acid, p-toluenesulfonic acid and 10-camphorsulfonic acid; and water, Among these, toluene, ethyl acetate, methanol, ethanol, i-propanol, acetic acid and hydrochloric acid aqueous solution are preferable, while methanol, ethanol, i-propanol and hydrochloric acid aqueous solution are particularly more preferable. These reaction solvents can be used alone or in combination.

The temperature condition is 40° C. or higher, preferably 40–200° C. and particularly more preferably 40–150° C.

In the after-treatment of Step 3, following completion of the reaction, a crude product can be obtained by performing a normal after-treatment procedure. The crude product is purified as necessary by active carbon, distillation, recrystallization, column chromatography and so forth to allow obtaining of the target optically active 1-(fluoro- or trifluoromethyl-substituted phenyl)ethylamine represented by the general formula [5] at high chemical purity.

In addition, according to the present invention, the above compound is in the R-form or S-form with respect to stereochemistry of the compound represented by the general formula [6], [4] or [7].

It was shown in Reference Examples 1 and 2 as well as in Examples 24, 25 and 26 that the heating conditions of the present hydrogenolysis are a more important factor than the amount of catalyst used and hydrogen pressure. Those results are summarized in the following Table 1 (runs 2, 3, 4, 5 and 6 correspond to the results of Reference Examples 1 and 2, Example 24, Example 25 and Example 26, respectively).

As Ar of the optically active secondary amine represented by the general formula [4], phenyl group, 1-naphthyl group and 2-naphthyl group are cited. Among these, phenyl group and 2-naphthyl group are preferable, while phenyl group is particularly more preferable.

TABLE 1

[Reaction scheme: fluorophenyl-substituted HN(CHMe)(CHMePh) → fluorophenyl-CH(NH$_2$)Me via Pd/C$_3$H$_2$, MeOH]

| run | Sub. (a.c.[2]*) | M (mol/l) | Pd/C (wt. % as Pd) | H$_2$ (MPa) | temp. (° C.) | additive (ratio vs. MeOH) | time (h) | conv. (%) (a:b[4]*) |
|---|---|---|---|---|---|---|---|---|
| 1* | o-F form (S) | 0.01 | 2 | 18 | 25 | AcOH (⅓) | — | 94[5]* (–) |
| 2 | p-F form (S, R mixture)[3]* | 0.01 | 2 | 7→3 | 25 | AcOH (⅓) | 21 | 43 (1:99) |
| 3 | p-F form (S, R mixture)[3]* | 0.01 | 2 | 7→5.5 | 25 | AcOH (⅓) | 21 | 72 (1:99) |
| 4 | p-F form (S, R mixture)[3]* | 1 | 0.123 | 0.5 | 60 | non | 21 | 73 (1:99) |
| 5 | p-F form (S, R mixture)[3]* | 1 | 0.05 | 0.5 | 100 | non | 21 | 84 (1:99) |
| 6 | p-F form (S, R mixture)[3]* | 1 | 0.075 | 0.8 | 60 | non | 21 | 72 (1:99) |

*Example of DE3819438,
[2]*Absolute configuration.
[3]*S:R = 93:7,
[4]*Selectivity at cleavage position,
[5]*Yield In addition, an even higher degree of optical purity can be obtained by converting the optically active 1-(3,5-bis-trifluoromethylphenyl)ethylamine represented by the formula [6], which is one of the target compounds, to a salt of an inorganic acid or organic acid, followed by purification by recrystallization at this stage. The purification method is described later.

Next, a detailed explanation is provided for a purification process that is another mode of the present invention.

The purification process of the present invention comprises two steps consisting of a step (Step 4) in which an optically active secondary amine of a synthetic intermediate obtained by asymmetric reduction is converted to a salt of an inorganic acid or organic acid and then purified by recrystallization, and a step (Step 5) in which optically active 1-(3,5-bis-trifluoromethylphenyl)ethylamine, which is one of the target compounds, is converted to a salt of an inorganic acid or organic acid and then purified by recrystallization.

In Step 4 of the present invention, the optically active secondary amine represented by the general formula [4] can be purified in an industrially efficient manner according to the method described below.

Namely, the optically active secondary amine produced in Step 2 and represented by the general formula [4] can be converted to a salt of an inorganic acid or organic acid and then purified by recrystallization.

The asterisks (*) of the optically active secondary amine represented by the general formula [4] represent chiral carbons, sax its stereochemistry includes a combination of a R—R form, S—R form, R—S form or S—S form (the absolute configuration before the hyphen represents the absolute configuration of the 1-(fluoro- or trifluoromethyl-substituted phenyl)ethyl group side, while the absolute configuration after the hyphen represents the absolute configuration of the α-arylethyl group side serving as a chiral auxiliary, and a chiral auxiliary is normally used in the R form or S form at 98% ee or more), and one in which the diastereomeric excess is 10% de or more can be used.

As the inorganic acid, there are cited carbonic acid, hydrochloric acid, sulfuric acid, nitric acid, hydrobromic acid, hydroiodic acid, phosphoric acid, boric acid, perchloric acid and the like. Among these, hydrochloric acid and hydrobromic acid are more preferable.

As the organic acid, there are cited aliphatic carboxylic acids such as acetic acid, propionic acid, butyric acid, isobutyric acid, valeric acid, isovaleric acid, hexanoic acid, heptanoic acid, cyclohexanecarboxylic acid, octanoic acid, phenylacetic acid and 3-phenylpropionic acid; haloalkylcarboxylic acids such as chloroacetic acid, dichloroacetic acid, trichloroacetic acid, fluoroacetic acid, difluoroacetic acid, trifluoroacetic acid, bromoacetic acid, iodoacetic acid, 2-chloropropionic acid and 3-chloropropionic acid; unsaturated carboxylic acids such as acrylic acid, crotonic acid, citraconic acid, maleic acid, fumaric acid and cis- or trans-cinnamic acid; aromatic carboxylic acids such as benzoic acid, o-, m- or p-toluic acid, o-, m- or p-fluorobenzoic acid, o-, m- or p-chlorobenzoic acid, o-, m or p-bromobenzoic acid, o-, m- or p-iodobenzoic acid, o, m- or p-hydroxybenzoic acid, o-, m- or p-anisic acid, o-, m- or p-aminobenzoic acid, o-, m- or p-nitrobenzoic acid, o-, m- or p-cyanobenzoic acid, o-, m- or p-benzenedicarboxylic acid (phthalic acid, isophthalic acid, terephthalic acid), α-, β- or γ-picolinic acid, 2,6-pyridinedicarboxylic acid and 1- or 2-naphthoic acid; sulfonic acids such as methanesulfonic acid, chloromethanesulfonic acid, trifluoromethanesulfonic acid, benzeneselfonic acid, p-toluenesulfonic acid and p-phenolsulfonic acid; optically active carboxylic acids such as lactic acid, malic acid, tartaric acid, dibenzoyltartaric acid, 2-phenylpropionic acid, mandelic acid, camphoric acid and cis-2-benzamidocyclohexanecarboxylic acid; optically active sulfonic acids such as phenylethanesulfonic acid and 10-camphorsulfonic acid; optically active phosphoric acids such as 2,2'-(1,1'-binaphthyl)phosphoric acid; optically active amino acids such as 4-aminobutyric acid, phenylglycine and aspartic acid; optically active N-acylamino acids such as pyroglutamic acid, N-acetyl-3,5-dibromo-tyrosine, N-acyl-phenylalanine, N-acyl-aspartic acid, N-acylglutamic acid and N-acylproline (wherein, N-acyl group represents acetyl group, benzyloxycarbonyl group, benzoyl group, benzenesulfonyl group, p-toluenesulfonyl group and the like), as well as other organic acids such as formic acid, oxalic acid, malonic acid, succinic acid, adipic acid, pimelic acid, cyanoacetic acid, citric acid, glycolic acid, glyoxylic acid, pyruvic acid, levulinic acid, oxaloacetic acid, mercaptoacetic acid, phenoxyacetic acid and picric acid. Although the optically active carboxylic acids, the optically active sulfonic acids, the optically active phosphoric acids, the optically active amino acids or the optically active N-acylamino acids exist in the R form or S form, their enantiomers may be suitably selected for use. Among these, phthalic acid, benzenesulfonic acid, p-toluenesulfonic acid and optically active mandelic acid are more preferable.

The amount of the inorganic acid or organic acid used may be 0–3 molar equivalents or more, preferably 0.3–5 molar equivalents, and particularly more preferably 0.3–3 molar equivalents, relative to the optically active secondary amine represented by the general formula [4].

The salt preparation method may be suitably determined according to the combination of the optically active secondary amine represented by the general formula [4] and the inorganic acid or organic acid, and it can normally be prepared by adding the secondary amine and the inorganic acid or organic acid directly to a recrystallization solvent followed by mixing, or by preparing each solution in advance and mixing the resulting solutions.

There are no particular restrictions on the recrystallization solvent provided it does not react with the optically active secondary amine represented by the general formula [4], the inorganic acid or organic acid, or salts formed therefrom. It may be suitably determined according to the diastereomeric excess prior to the purification or the target excess rate and recovery rate, etc. of the diastereomer after the purification. As the recrystallization solvent, there are cited aliphatic hydrocarbons such as n-pentane, n-hexane, c-hexane and n-heptane; aromatic hydrocarbons such as benzene, toluene, ethylbenzene, xylene and mesitylene; halogenated hydrocarbons such as methylene chloride, chloroform and 1,2-dichloroethane; ethers such as diethyl ether, tetrahydrofuran, t-butylmethyl ether and 1,4-dioxane; ketones such as acetone, methylethyl ketone and methylisobutyl ketone; esters such as ethyl acetate and n-butyl acetate; nitriles such as acetonitrile and propionitrile; alcohols such as methanol, ethanol, n-propanol and i-propanol and n-butanol; and water. Among these, n-hexane, n-heptane, toluene, methylene chloride, t-butylmethyl ether, acetone, ethyl acetate, acetonitrile, methanol, ethanol, n-propanol and i-propanol are more preferable. These recrystallization solvents can be used alone or in combination.

There are no particular restrictions on the amount of the recrystallization solvent used provided it is within a range over which the salt prior to the purification either completely or partially dissolves when heated. It may be suitably determined according to the diastereomeric excess prior to the purification or the target excess rate and recovery rate, etc. of the diastereomer after purification. Normally, the amount of the recrystallization solvent used may be 1 volume or more, preferably 1–100 volumes, and particularly more preferably 1–50 volumes, relative to the salt of the optically active secondary amine represented by the general formula [4].

Crystals can be precipitated smoothly and efficiently by adding seed crystal during the recrystallization procedure. For the amount of seed crystal used, preferably 1/10–1/10000 the weight, and particularly more preferably 1/20–1/5000 the weight, of the salt is added relative to the salt prior to purification.

Temperature conditions can be suitably determined according to the boiling point and freezing point of the solvent used, and the salt prior to purification can normally be dissolved at a temperature ranging from room temperature (25° C.) to a temperature near the boiling point of the recrystallization solvent, and the crystals can be precipitated at a temperature from −40° C. to 80° C.

Since the diastereomeric excess of the precipitated crystals increases in the recrystallization procedure, a highly pure salt of the optically active secondary amine represented by the general formula [4] can be obtained by recovering the precipitated crystals by filtration and so forth. In addition, that of even higher purity can be obtained by repeating the recrystallization procedure. The target optically active 1-(fluoro- or trifluoromethyl-substituted phenyl)ethylamine can be obtained at high optical purity, without the occurrence of racemization, by subjecting the resulting salt either directly or after converting to a free base with an aqueous alkaline solution to hydrogenolysis. However, in the case of performing hydrogenolysis directly on the resulting salt, since the target optically active 1-(fluoro- or trifluoromethyl-substituted phenyl)ethylamine is obtained in the form of the salt of the corresponding inorganic acid or organic acid, the optically active amine can be recovered as a free base by neutralizing with an aqueous alkaline solution and extracting with an organic solvent following completion of the reaction. In addition, the resulting crude product of the optically active amine can be purified as necessary using active carbon, distillation, recrystallization, column chromatography and so forth.

In addition, the optically active 1-(3,5-bis-trifluoromethylphenyl)ethylamine represented by the formula [6] can be purified in an industrially efficient manner in Step 5 of the present invention according to the method described below.

Namely, the optically active 1-(3,5-bis-trifluoromethylphenyl)ethylamine produced in Step 3, represented by the formula [6], can be purified by recrystallization after converting to a salt of an inorganic acid or organic acid.

The asterisk (*) of the optically active 1-(3,5-bis-trifluoromethylphenyl)ethylamine represented by the formula [6] represents a chiral carbon, its stereochemistry includes the R form or S form, and one in which the enantiomeric excess is 10% ee or more can be used.

As the inorganic acid or organic acid, those listed in Step 4 are cited. Among these, p-toluenesulfonic acid, optically active mandelic acid and optically active tartaric acid are more preferable.

In addition, the amount of inorganic acid or organic acid used, the salt preparation method, the recrystallization solvent, the amount of recrystallization solvent used, the addition of seed crystal and the temperature conditions are the same as those indicated in Step 4. However, the phrases, "the optically active secondary amine represented by the general formula [4]" and "the diastereomeric excess" should be respectively read as "the optically active 1-(3, 5-bis-trifluoromethylphenyl)ethylamine represented by the formula [6]" and "the enantiomeric excess".

Since the enantiomeric excess of the precipitated crystals increases in the recrystallization procedure, a highly pure salt of the optically active 1-(3,5-bis-trifluoromethylphenyl) ethylamine represented by the formula [6] can be obtained by recovering the precipitated crystals by filtration and so forth. In addition, that of even higher purity can be obtained by repeating the recrystallization procedure. The optically active amine can be recovered as a free base by neutralizing the resulting salt with an aqueous alkaline solution and by extracting with an organic solvent. In addition, the crude product of the resulting optically active amine can be purified as necessary using active carbon, distillation, recrystallization, column chromatography and so forth.

EXAMPLES

Although the following provides a detailed explanation of the mode for carrying out the present invention through the examples indicated below, the present invention is not limited to these examples.

Conversion, selectivity at the cleavage position (a:b), diastereomer ratio or optical purity indicated in the examples and reference examples was determined by chiral GC (CP-Chirasil-Dex CB).

Examples 1–9

3,5-Bis-Trifluoromethyl-Substituted Form

Example 1

Step 1: Dehydration and Condensation 10 g (39.06 mmol, 1 eq) of 3,5-bis-trifluoromethylphenylmethyl ketone, 4.96 g (41.02 mmol, 1.05 eq) of (S)-1-phenylethylamine and 0.37 g (1.95 mmol, 0.05 eq) of p-toluenesulfonic acid monohydrate were dissolved in 100 ml of toluene, followed by reflux while heating for 24 hours and then removal of the by-product water with a Dean-Stark tube. Following completion of the reaction, the reaction liquid was washed with saturated sodium bicarbonate aqueous solution and dried with anhydrous magnesium sulfate followed by filtration, concentration and vacuum drying to quantitatively obtain the crude product of an optically active amine (3a) represented by the following formula:

[Chemical 27]

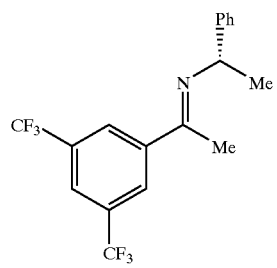

[3a]

The crude product was used for asymmetric reduction without purifying.

$^1$H-NMR (TMS, CDCl$_3$): 1.55 (d, 6.4 Hz, 3H), 2.33 (s, 3H), 4.87 (q, 6.4 Hz, 1H), 7.24 (t, 7.8 Hz, 1H), 7.35 (t, 7.8 Hz, 2H), 7.45 (d, 7.8 Hz, 2H), 8.31 (s, 1H), 8.38 (s, 2H).

Examples 2–8

Step 2: Asymmetric Reduction
(Typical Experimental Procedure)

359 mg (1 mmol, 1 eq) of the optically active imine (3a) produced in Example 1 were dissolved in 5 ml of various alcohols or tetrahydrofuran, and after cooling to a set temperature, 38 mg of sodium borohydride or 38 mg (1 mmol, 1 eq) of lithium aluminum hydride were added followed by stirring for a predetermined amount of time. Following completion of the reaction, 0.1 N hydrochloric acid was added to the reaction liquid to terminate the reaction followed by extraction with ethyl acetate, washing with 0.5 N sodium hydroxide, drying with anhydrous magnesium sulfate, filtration, concentration and vacuum drying to obtain a crude product of the optically active secondary amine (4a). Conversion and diastereomer ratio of the crude product were determined by chiral GC. The reaction conditions and the results of each example are summarized in Table 2.

TABLE 2

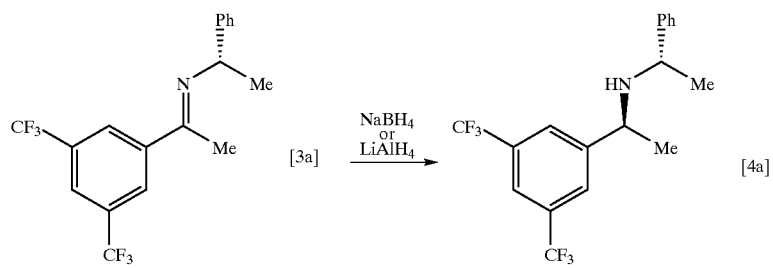

| Example | Reaction solvent | Hydride reducing agent | Reaction temp. (° C.) | Reaction time (h) | Conversion (%) | Diastereomer ratio (S-S:R-S) |
|---|---|---|---|---|---|---|
| 2 | Methanol | NaBH$_4$ | 0 | 2 | 100 | 5.4:1 |
| 3 | i-propanol | MaBH$_4$ | 0 | 3 | 100 | 7.2:1 |
| 4 | i-propanol | NaBH$_4$ | −40 | 1 | 91 | 6.6:1 |
| 5 | Ethanol | NaBH$_4$ | Room temp. | 20 | 100 | 5.7:1 |

TABLE 2-continued

| Example | Reaction solvent | Hydride reducing agent | Reaction temp. (° C.) | Reaction time (h) | Conversion (%) | Diastereomer ratio (S-S:R-S) |
|---|---|---|---|---|---|---|
| 6 | Ethanol | NaBH$_4$ | −10 | 2 | 100 | 6.9:1 |
| 7 | Ethanol | NaBH$_4$ | −40 | 4 | 100 | 7.8:1 |
| 8 | Tetrahydrofuran | LiAlH$_4$ | Room temp. | 14 | 47 | 2.1:1 |

$^1$H-NMR (TMS, CDCl$_3$): 1.28 (d, 6.5 Hz, 3H), 1.29 (d, 6.4 Hz, 3H) 1.58 (br, 1H), 3.39 (q, 6.5 Hz, 1H), 3.65 (q, 6.4 Hz, 1H), 7.05–7.44 (m, 5H), 7.70 (s, 2H), 7.76 (s, 1H).

Example 9

Step 3: Hydrogenolysis 181 mg (0.5 mmol) of the crude product of optically active secondary amine (4a) produced in Example 7 and 18 mg (0.25 wt %) of 5% palladium/active carbon (water content: 50 wt %) were added to 2 ml of ethanol followed by setting the hydrogen pressure to 0.2 MPa and stirring for 12 hours at 55° C. Following completion of the reaction, the reaction liquid was filtered with Celite, concentrated and vacuum dried to obtain 96 mg of a crude product of the optically active 1-(3,5-bis-trifluoromethylphenyl)ethylamine (5a) represented by the following formula:

[Chemical 28]

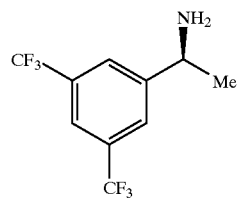

The yield was 75%. Conversion, selectivity at the cleavage position (the previously mentioned a:b) and optical purity of the crude product were determined by chiral GC, and found to be 99%, a:b=1:99 and 76% ee, respectively.

Examples 10–12

2-Trifluoromethyl-Substituted Form

Example 10

Step 1: Dehydration and Condensation 5.02 g (26.70 mmol, 1 eq) of 2-trifluoromethylphenylmethyl ketone, 3.67 g (30.33 mmol, 1.14 eq) of (S)-1-phenylethylamine and 0.55 g (4.04 mmol, 0.15 eq) of zinc chloride were dissolved in 27 ml of toluene, followed by reflux while heating for 43.5 hours and then removal of the by-product water with a Dean-Stark tube. Following completion of the reaction, the reaction liquid was washed once with 5% aqueous sodium hydroxide, three times with 1.5 N aqueous ammonium chloride and once with water. The recovered organic layer was dried with anhydrous sodium sulfate followed by filtration, concentration and vacuum drying to obtain 6.64 g of a crude product of the optically active imine (3b) represented by the following formula;

[Chemical 29]

Conversion of the crude product was determined by chiral GC and found to be 77%. The crude product was confirmed to be a mixture of three isomers, including an atrop isomer, by $^1$H and $^{19}$F-NMR. The crude product was purified by distillation to remove unreacted 2-trifluoromethylphenylmethyl ketone and obtain 3.97 g of a purified product (yield: 51%). Changes in the isomer ratio were observed before and after the distillation purification. The results of GC purity and isomer ratio are summarized in Table 3.

TABLE 3

| | GC purity (%) | Isomer $^{19}$F-NMR chemical shift (ppm) 103.7 102.0 101.9 |
|---|---|---|
| Before distillation (crude product) | 76.9 | 2.55:2.47:1 |
| After distillation (purified product) | 99.5 | 1.09:1.95:1 |

Boiling point: 116–118° C./2 mmHg

¹H-NMR (TMS, CDCl₃): 1.32 (d, 6.4 Hz) & 1.42 (d, 6.4 Hz) & 1.56 (d, 6.4 Hz)/total 3H, 2.20 (s) & 2.32 (s) & 2.34 (s)/total 3H, 4.06 (q, 6.4 Hz) & 4.08 (d, 6.4 Hz) & 4.81 (d, 6.4 Hz)/total 1H, 6.70–7.80 (m, 9H).

¹⁹F-NMR (C₆F₆, CDCl₃): 103.7, 102.0, 101.9.

Example 11

Step 2: Asymmetric Reduction 1.42 g (4–89 mmol, 1 eq) of the purified product of the optically active imine (3b) produced in Example 10 were dissolved in 4 ml of methanol, and after cooling to 0° C., 0.42 g (10.97 mmol, 2.24 eq) of sodium borohydride were added followed by stirring for 5 hours at the same temperature and then for 62 hours at room temperature. The reaction was terminated by adding 1 N aqueous hydrochloric acid to the reaction mixture liquid followed by making it alkaline with 1 N aqueous sodium hydroxide, extracting with toluene, washing with water, drying with anhydrous sodium sulfate, filtering, concentrating and vacuum drying to obtain 1.53 g of a crude product of the optically active secondary amine (4b) represented by the following formula:

[Chemical 30]

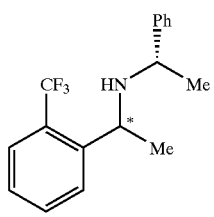

[4b]

Conversion and diastereomer ratio of the crude product were determined by chiral GC and found to be 56% and 59:41, respectively.

¹H-NMR (TMS, CDCl₃) of major diastereomer: 1.26 (d, 6.8 Hz, 3H), 1.36 (d, 6.8 Hz, 3H), 1.57 (br, 1H), 3.48 (q, 6.8 Hz, 1H), 4.06 (q, 6.8 Hz, 1H), 6.70–8.00 (m, 9H).

¹H-NMR (TMS, CDCl₃) of minor diastereomer: 1.26 (d, 6.5 Hz, 3H), 1.32 (d, 6.5 Hz, 3H), 1.57 (br, 1H), 3.63 (d, 6.5 Hz, 1H), 4.33 (q, 6.5 Hz, 1H), 6.70–8.00 (m, 9H).

Example 12

Step 3: Hydrogenolysis 440 mg (1.50 mmol) of the crude product of the optically active secondary amine (4b) produced in Example 11 and 8.8 mg (0.05 wt %) of 5% palladium/active carbon (water content; 50 wt %) were added to 1.5 ml of methanol, followed by setting the hydrogen pressure to 0.5 MPa and stirring for 5 days at 60° C. Following completion of the reaction, the reaction liquid was filtered with Celite, concentrated and vacuum dried to obtain a crude product of the optically active 1-(2-trifluoromethylphenyl) ethylamine (5b) represented by the following formula:

[Chemical 31]

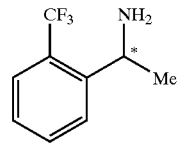

[5b]

Conversion, selectivity at the cleavage position (the previously mentioned a:b) and optical purity of the crude product were determined by chiral GC and found to be 100%, a:b=1:99 and 18% ee, respectively.

¹H-NMR (TMS, CDCl₃): 1.41 (d, 6.6 Hz, 3H), 1.56 (br, 2H), 4.56 (q, 6.6 Hz, 1H), 7.33 (t, 7.9 Hz, 1H), 7.57 (t, 1.9 Hz, 1H), 7.61 (d, 7.9 Hz, 1H), 7.74 (d, 7.9 Hz, 1H).

Examples 13–15

3-Trifluoromethyl-Substituted Form

Example 13

Step 1: Dehydration and Condensation 5.02 g (26.70 mmol, 1 eq) of 3-trifluoromethylphenylmethyl ketone, 3.67 g (30.33 mmol, 1.14 eq) of (S)-1-phenylethylamine and 0.11 g (0.81 mmol, 0.03 eq) of zinc chloride were dissolved in 27 ml of toluene, followed by refluxing while heating for 8 hours and removing the by-product water with a Dean-Stark tube. Following completion of the reaction, the reaction liquid was washed once with 5% aqueous sodium hydroxide, 3 times with 1.5 N aqueous ammonium chloride and once with water. The recovered organic layer was dried with anhydrous sodium sulfate, filtered, concentrated and vacuum dried to obtain 8.22 g of a crude product of the optically active imine (3c) represented by the following formula;

[Chemical 32]

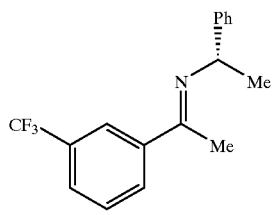

[3c]

Conversion of the crude product was determined by chiral GC and found to be 96%.

¹H-NMR (TMS, CDCl₃): 1.54 (d, 6.6 Hz, 3H), 2.29 (s, 3H), 4.85 (q, 6.6 Hz, 1H), 7.24 (t, 7.8 Hz, 1H), 7.34 (t, 7.8 Hz, 2H), 7.46 (d, 7.8 Hz, 2H), 7.49 (t, 8.0 Hz, 1H), 7.63 (d, 8.0 Hz, 1H), 8.03 (d, 8.0 Hz, 1H), 8.09 (s, 1H).

Example 14

Step 2: Asymmetric Reduction 8.22 g (25.63 mmol, 1 eq) of the crude product of the optically active imine (3c) produced in Example 13 were dissolved in 22 ml of methanol, and after cooling to 0° C., 1.07 g (28.16 mmol, 1.10 eq) of sodium borohydride were added followed by stirring for 6.75 hours at the same temperature. 1 N aqueous hydrochloric acid was added to the reaction mixture liquid to stop the reaction followed by making it alkaline with 1 N aqueous sodium hydroxide, extracting with toluene, washing with water, drying with anhydrous sodium sulfate, filtering, concentrating and vacuum drying to obtain a crude product of the optically active secondary amine (4c) represented by the following formula;

[Chemical 33]

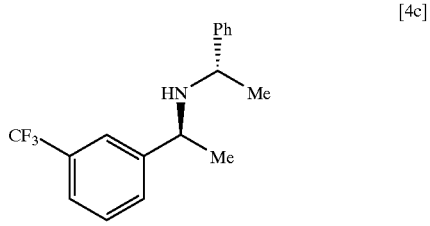

[4c]

Conversion and diastereomer ratio of the crude product were determined by chiral GC and found to be 100% and S—S:R—S=86:14, respectively. The crude product was then purified by column chromatography (silica gel, ethyl acetate:n-hexane=1:6) to obtain 7.11 g of a purified product (yield: 95%).

S—S form $^1$H-NMR (TMS, CDCl$_3$): 1.27 (d, 6.7 Hz, 3H), 1.28 (d, 6.7 Hz, 3H), 1.57 (br, 1H), 3.43 (q, 6.7 Hz, 1H), 3.57 (q, 6.7 Hz, 1H), 7.14–7.56 (m, 9H).

R—S form $^1$H-NMR (TMS, CDCl$_3$): 1.35 (d, 6.5 Hz, 3H), 1.36 (d, 6.5 Hz, 3H), 1.57 (br, 1H), 3.76 (q, 6.5 Hz, 1H), 3.82 (q, 6.5 Hz, 1H), 7.14–7.56 (m, 9H).

Example 15

Step 3: Hydrogenolysis 440 mg (1.50 mmol) of the purified product of the optically active secondary amine (4c) produced in Example 14 and 8.8 mg (0.05 wt %) of 5% palladium/active carbon (water content: 50 wt %) were added to 1.5 ml of methanol, followed by setting the hydrogen pressure to 0.5 MPa and stirring for 12 hours at 60° C. Following completion of the reaction, the reaction mixture was filtered with Celite, concentrated and vacuum dried to obtain a crude product of the optically active 1-(3-trifluoromethylphenyl)ethylamine (5c) represented by the following formula;

[Chemical 34]

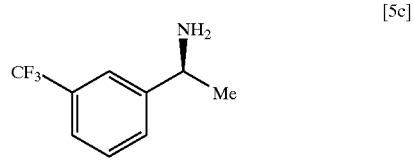

[5c]

Conversion, selectivity at the cleavage position (the previously mentioned a:b) and optical purity of the crude product were determined by chiral GC and found to be 76%, a:b=3:97 and 72% ee, respectively.

$^1$H-NMR (TMS, CDCl$_3$): 1.41 (d, 6.7 Hz, 3H), 1.55 (br, 2H), 4.20 (q, 6.7 Hz, 1H), 7.40–7.59 (m, 3H), 7.61 (s, 1H).

Examples 16–18

4-Trifluoromethyl-Substituted Form

Example 16

Step 1: Dehydration and Condensation 5.02 g (26.70 mmol, 1 eq) of 4-trifluoromethylphenylmethyl ketone, 3.67 g (30.33 mmol, 1.14 eq) of (S)-1-phenylethylamine and 0.11 g (0.81 mmol, 0.03 eq) of zinc chloride were dissolved in 27 ml of toluene, followed by refluxing while heating for 15 hours and removing the by-product water with a Dean-Stark tube. Following completion of the reaction, the reaction liquid was washed once with 5% aqueous sodium hydroxide, 3 times with 1.5 N aqueous ammonium chloride and once with water. The recovered organic layer was dried with anhydrous sodium sulfate, filtered, concentrated and vacuum dried to obtain 8.20 g of a crude product of the optically active imine (3d) represented by the following formula:

[Chemical 35]

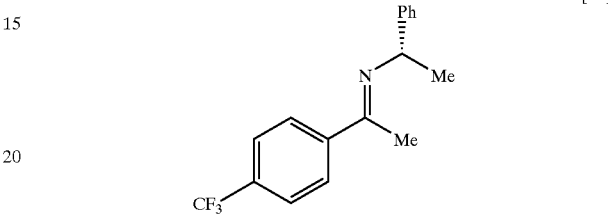

[3d]

Conversion of the crude product was determined by chiral GC and found to be 99%.

$^1$H-NMR (TMS, CDCl$_3$): 1.54 (d, 6.6 Hz, 3H), 2.29 (s, 3H), 4.85 (q, 6.6 Hz, 1H), 7.24 (t, 7.6 Hz, 1H), 7–34 (t, 7.6 Hz, 2H), 7.46 (d, 7.6 Hz, 2H), 7.63 (d, 8.3 Hz, 2H), 7.94 (d, 8.3 Hz, 2H).

Example 17

Step 2: Asymmetric Reduction 8.20 g (26.43 mmol, 1 eq) of the crude product of the optically active imine (3d) produced in Example 16 were 'dissolved in 22 ml of methanol, and after cooling to 0° C., 1.06 g (27.89 mmol, 1.06 eq) of sodium borohydride were added, followed by stirring for 5.5 hours at the same temperature. 1 N aqueous hydrochloric acid was added to the reaction mixture liquid to stop the reaction, followed by making it alkaline with 1 N aqueous sodium hydroxide, extracting with toluene, washing with water, drying with anhydrous sodium sulfate, filtering, concentrating and vacuum drying to obtain a crude product of the optically active secondary amine (4d) represented by the following formula:

[Chemical 36]

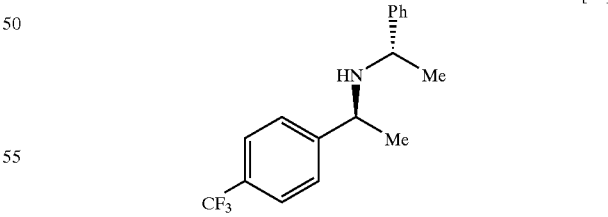

[4d]

Conversion and diastereomer ratio of the crude product were determined by chiral GC and found to be 100% and S—S:R—S=84:16, respectively.

S—S form $^1$H-NMR (TMS, CDCl$_3$): 1.27 (d, 6.6 Hz, 3H), 1.29 (d, 6.6 Hz, 3H), 1.59 (br, 1H), 3.45 (q, 6.6 Hz, 1H), 3,57 (q, 6.6 Hz, 1H), 7.12–7.67 (m, 9H).

R—S form $^1$H-NMR (TMS, CDCl$_3$): 1.37 (d, 6.8 Hz, 6H), 1.59 (br, 1H), 3.76 (q, 6.8 Hz, 1H), 3.84 (q, 6.8 Hz, 1H), 7.12–7.67 (m, 9H).

Example 18

Step 3: Hydrogenolysis 440 mg (1.50 mmol) of the crude product of the optically active secondary amine (4d) produced in Example 17 and 8.8 mg (0.05 wt %) of 5% palladium/active carbon (water content: 50 wt %) were added to 1.5 ml of methanol, followed by setting the hydrogen pressure to 0.5 MPa and stirring for 12.7 hours at 60° C. Following completion of the reaction, the reaction liquid was filtered with Celite, concentrated and vacuum dried to obtain a crude product of the optically active 1-(4-trifluoromethylphenyl)ethylamine (5d) represented by the following formula:

[Chemical 37]

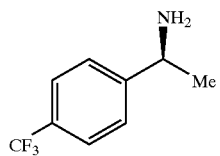

[5d]

Conversion, selectivity at the cleavage position (the previously mentioned a:b) and optical purity of the crude product were determined by chiral GC and found to be 58%, a:b=3:97 and 68% ee, respectively.

$^1$H-NMR (TMS, CDCl$_3$): 1.40 (d, 6.8 Hz, 3H), 1.60 (br, 2H), 4.19 (q, 6.8 Hz, 1H), 7.46 (d, 8.2 Hz, 2H), 7.59 (d, 8.2 Hz, 2H).

Examples 19–21

3-Fluoro-Substituted Form

Example 19

Step 1: Dehydration and Condensation 4.00 g (28.96 mmol, 1 eq) of 3-fluorophenylmethyl ketone, 3.86 g (31.85 mmol, 1.10 eq) of (S)-1-phenylethylamine and 0.12 g (0.88 mmol, 0.03 eq) of zinc chloride were dissolved in 29 ml of toluene, followed by refluxing while heating for 15 hours and removing the by-product water with a Dean-Stark tube. Following completion of the reaction, the reaction liquid was washed once with 5% aqueous sodium hydroxide, 3 times with 1.5 N aqueous ammonium chloride and once with water. The recovered organic layer was dried with anhydrous sodium sulfate, filtered, concentrated and vacuum dried to obtain 7.46 g of a crude product of the optically active imine (3e) represented by the following formula:

[Chemical 38]

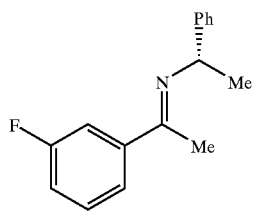

[3e]

Conversion of the crude product was determined by chiral GC and found to be 100%.

$^1$-NMR (TMS, CDCl$_3$): 1.53 (d, 6.6 Hz, 3H), 2.25 (s, 3H), 4.83 (q, 6.6 Hz, 1H), 7.00–7.65 (Ar—H, 9H).

Example 20

Step 2: Asymmetric Reduction 7.46 g (28.96 mmol, 1 eq) of the crude product of the optically active imine (38) produced in Example 19 were dissolved in 22 ml of methanol, and after cooling to 0° C., 1.10 g (29.08 mmol, 1.00 eq) of sodium borohydride were added, followed by stirring for 6 hours at the same temperature. 1 N aqueous hydrochloric acid was added to the reaction mixture liquid to stop the reaction, followed by making it alkaline with 1 N aqueous sodium hydroxide, extracting with toluene, washing with water, drying with anhydrous sodium sulfate, filtering, concentrating and vacuum drying to obtain 7.08 g of a crude product of the optically active secondary amine (4e) represented by the following formula:

[Chemical 39]

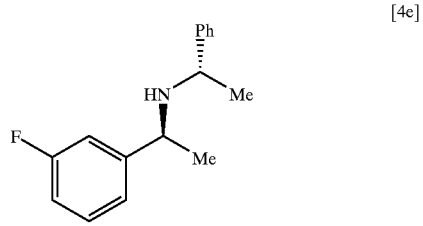

[4e]

Conversion and diastereomer ratio of the crude product were determined by chiral GC and found to be 100% and S-S:R—S=86:14, respectively.

S-S form $^1$H-NMR (TMS, CDCl$_3$): 1.25 (d, 6.8 Hz, 3H), 1.28 (d, 6.8 Hz, 3H), 1.57 (br, 1H), 3.40–3.55 (m, 2H), 6.80–7.45 (Ar—H, 9H).

R-S form $^1$H-NMR (TMS, CDCl$_3$): 1.33 (d, 6.8 Hz, 3H), 1.35 (d, 6.8 Hz, 3H), 1.57 (br, 1H), 3.70–3.80 (m, 2H), 6.80–7.45 (Ar—H, 9H).

Example 21

Step 3: Hydrogenolysis 375 mg (1.54 mmol) of the crude product of the optically active secondary amine (4e) produced in Example 20 and 6.9 mg (0.05 wt % as Pd) of 5% palladium/active carbon (water content. 50 wt %) were added to 1.5 ml of methanol, followed by setting the hydrogen pressure to 0.5 MPa and stirring for 21 hours at 60° C. Following completion of the reaction, the reaction liquid was filtered with Celite, concentrated and vacuum dried to obtain a crude product of the optically active 1-(3-fluorophenyl)ethylamine (5e) represented by the following formula:

[Chemical 40]

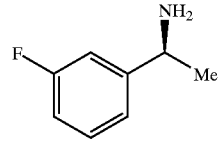

[5e]

Conversion, selectivity at the cleavage position (the previously mentioned a:b) and optical purity of the crude product were determined by chiral GC and found to be 58%, a:b=0:100 and 72% ee, respectively.

$^1$H-NMR (TMS, CDCl$_3$): 1.40 (d, 6.6 Hz, 3H), 2.80 (br, 2H), 4.10 (q, 6.6 Hz, 1H), 6.86–7.42 (Ar—H, 4H).

Examples 22–26

4-Fluoro-Substituted Form

Example 22

Step 1: Dehydration and Condensation 20.00 g (144.78 mmol, 1 eq) of 4-fluorophenylmethyl ketone, 19.30 g (159.27 mmol, 1.10 eq) of (S)-1-phenylethylamine and 0.60 g (4.40 mmol, 0.03 eq) of zinc chloride were dissolved in 145 ml of toluene, followed by refluxing while heating for 19 hours and removing the by-product water with a Dean-Stark tube. Following completion of the reaction, the reaction liquid was washed once with 5% aqueous sodium hydroxide, 3 times with 1.5 N aqueous ammonium chloride and once with water. The recovered organic layer was dried with anhydrous sodium sulfate, filtered, concentrated and vacuum dried to obtain 35.00 g of a crude product of the optically active mine (3f) represented by the following formula:

[Chemical 41]

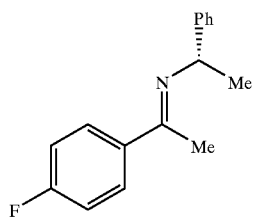

[3f]

Conversion of the crude product was determined by chiral GC and found to be 98%.

$^1$H-NMR (TMS, CDCl$_3$): 1.53 (d, 6.6 Hz, 3H), 2.25 (s, 3H), 4.82 (q, 6.6 Hz, 1H), 7.00–7.50 (Ar—H, 7H), 7.80–7.90 (Ar—H, 2H).

Example 23

Step 2: Asymmetric Reduction 35.00 g (144.78 mmol, 1 eq) of the crude product of the optically active imine (3f) produced in Example 22 were dissolved in 120 ml of methanol, and after cooling to 0° C., 5.50 g (145.39 mmol, 1.00 eq) of sodium borohydride were added followed by stirring for S hours at the same temperature. 1 N aqueous hydrochloric acid was added to the reaction mixture liquid to stop the reaction, followed by making it alkaline with 1 N aqueous sodium hydroxide, extracting with toluene, washing with water, drying with anhydrous sodium sulfate, filtering, concentrating and vacuum drying to obtain 35.34 g of a crude product of the optically active secondary amine (4f) represented by the following formula:

[Chemical 42]

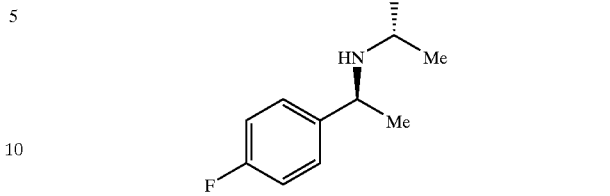

[4f]

Conversion and diastereomer ratio of the crude product were determined by chiral GC and found to be 100% and S-S:R-S=93:7, respectively.

S-S form $^1$H-NMR (TMS, CDCl$_3$): 1.24 (d, 6.4 Hz, 3H), 1.27 (d, 6.4 Hz, 3H), 1.60 (br, 1H), 3.45 (q, 6.4 Hz, 1H), 3.49 (q, 6.4 Hz, 1H), 6.90–7.50 (Ar—H, 9H).

R-S form $^1$H-NMR (TMS, CDCl$_3$): 1.32 (d, 6.8 Hz, 3H), 1.35 (d, 6.8 Hz, 3H), 1.60 (br, 1H), 3.74 (q, 6.8 Hz, 2H), 6.90–7.50 (Ar—H, 9H).

Example 24

Step 3: Hydrogenolysis (Corresponding to Table 1, Run 4)

367 mg (1.51 mmol) of the crude product of the optically active secondary amine (4f) produced in Example 23 and 18.0 mg (0.123 wt % as Pd) of 5% palladium/active carbon (water content: 50 wt %) were added to 1.5 ml of methanol, followed by setting the hydrogen pressure to 0.5 MPa and stirring for 21 hours at 60° C. Following completion of the reaction, the reaction liquid was filtered with Celite, concentrated and vacuum dried to obtain a crude product of the optically active 1-(4-fluorophenyl)ethylamine (5f) represented by the following formula:

[Chemical 43]

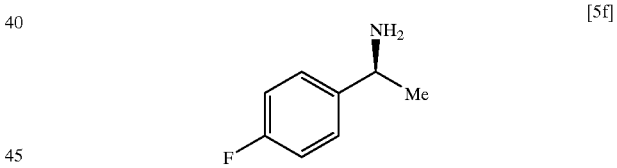

[5f]

Conversion, selectivity at the cleavage position (the previously mentioned a:b) and optical purity of the crude product were determined by chiral GC and found to be 73%, a:b=1:99 and 86% ee, respectively.

$^1$H-NMR (TMS, CDCl$_3$): 1.39 (d, 6.6 Hz, 3H), 2.10 (br, 2H), 4.11 (q 6.6 Hz, 1H), 7.12–7.38 (Ar—H, 4H).

Example 25

Step 3: Hydrogenolysis (Corresponding to Table 1, Run 5)

365 mg (1.50 mmol) of the crude product of the optically active secondary amine (4f) produced in Example 23 and 7.3 mg (0.05 wt % as Pd) of 5% palladium/active carbon (water content: 50 wt %) were added to 1.5 ml of methanol, followed by setting the hydrogen pressure to 0.5 MPa and stirring for 21 hours at 100° C. Following completion of the reaction, the reaction liquid was filtered with Celite, concentrated and vacuum dried to obtain a crude product of the optically active 1-(4-fluorophenyl)ethylamine (5f) represented by the following formula:

[Chemical 44]

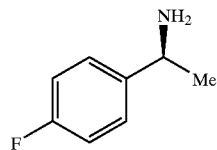

[5f]

Conversion, selectivity at the cleavage position (the previously mentioned a:b) and optical purity of the crude product were determined by chiral GC and found to be 84%, a:b=1:99 and 86% ee, respectively.

Example 26

Step 3: Hydrogenolysis (Corresponding to Table 1, Run 6)

365 mg (1.50 mmol) of the crude product of the optically active secondary amine (4f) produced in Example 23 and 11.0 mg (0.075 wt % as Pd) of 5% palladium/active carbon (water content: 50 wt %) were added to 1.5 ml of methanol, followed by setting the hydrogen pressure to 0.8 MPa and stirring for 21 hours at 60° C. Following completion of the reaction, the reaction liquid was filtered with Celite, concentrated and vacuum dried to obtain a crude product of the optically active 1-(4-fluorophenyl )ethylamine (5) represented by the following formula:

[Chemical 45]

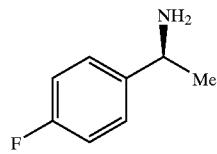

[5f]

Conversion, selectivity at the cleavage position (the previously mentioned a:b) and optical purity of the crude product were determined by chiral CC and found to be 72%, a:b=1:99 and 86% ee, respectively.

Reference Example 1

Step 3: Hydrogenolysis (Corresponding to Table 1, Run 2)

365 mg (1.50 mmol) of the crude product of the optically active secondary amine (4f) produced in Example 23 and 300.0 mg (2 wt % as Pd) of 5% palladium/active carbon (water content: 50 wt %) were added to 112.5 ml of methanol and 37.5 ml of acetic acid, followed by setting the hydrogen pressure to 7 MPa and stirring for 21 hours at 25° C. (internal pressure at completion of the reaction: 3 MPa). Following completion of the reaction, the reaction liquid was filtered with Celite, concentrated and vacuum dried to obtain a crude product of the optically active 1-(4-fluorophenyl)ethylamine (5f) represented by the following formula:

[Chemical 46]

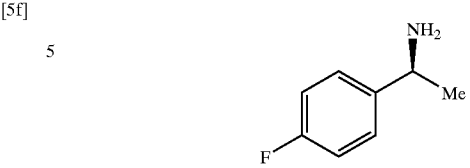

[5f]

Conversion, selectivity at the cleavage position (the previously mentioned a:b) and optical purity of the crude product were determined by chiral GC and found to be 43%, a:b=1:99 and 86% ee, respectively.

Reference Example 2

Step 3: Hydrogenolysis (Corresponding to Table 16 Run 3)

365 mg (1.50 mmol) of the crude product of the optically active secondary amine (4f) produced in Example 23 and 300.0 mg (2 wt % as Pd) of 5% palladium/active carbon (water content; 50 wt %) were added to 112.5 ml of methanol and 37.5 ml of acetic acid, followed by setting the hydrogen pressure to 7 MPa and stirring for 21 hours at 25° C. (internal pressure at completion of the reaction: 5.5 MPa). Following completion of the reaction, the reaction liquid was filtered with Celite, concentrated and vacuum dried to obtain a crude product of the optically active 1-(4-fluorophenyl)ethylamine (5f) represented by the following formula:

[Chemical 47]

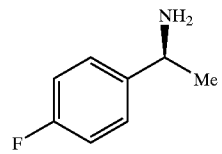

[5f]

Conversion, selectivity at the cleavage position (the previously mentioned a:b) and optical purity of the crude product were determined by chiral GC and found to be 72%, a:b=1:99 and 86% ee, respectively.

Examples 27–29

3,5-Difluoro-Substituted Form

Example 27

Step 1: Dehydration and Condensation 2.99 g (19.16 mmol, 1 eq) of 3,5-difluorophenylmethyl ketone, 2.57 g (21.19 mmol, 1.11 eq) of (S)-1-phenylethylamine and 0.08 g (0.58 mmol, 0.03 eq) of zinc chloride were dissolved in 19 ml of toluene, followed by refluxing while heating for 16 hours and removing the by-product water with a Dean-Stark tube. Following completion of the reaction, the reaction liquid was washed once with 5% aqueous sodium hydroxide, 3 times with 1.5 N aqueous ammonium chloride and once with water. The recovered organic layer was dried with anhydrous sodium sulfate, filtered, concentrated and vacuum dried to obtain 4.98 g of a crude product of the optically active imine (3g) represented by the following formula:

[Chemical 48]

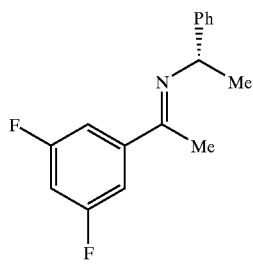

[3g]

Conversion of the crude product was determined by chiral GC and found to be 100%.

$^1$H-NMR (TMS, CDCl$_3$): 1.52 (d, 6.6 Hz, 3H), 2.23 (s, 3H), 4.82 (q, 6.6 Hz, 1H), 6.77–6.86 (Ar—H, 1H), 7.12–7.48 (Ar—H, 7H).

Example 28

Step 2: Asymmetric Reduction 4.98 g (19.16 mmol, 1 eq) of the crude product of the optically active imine (3g) produced in Example 27 were dissolved in 16 ml of methanol, and after cooling to 0° C., 0.73 g (19.30 mmol, 1.01 eq) of sodium borohydride were added followed by stirring for 3 hours at the same temperature. 1 N aqueous hydrochloric acid was added to the reaction mixture liquid to stop the reaction, followed by making it alkaline with 1 N aqueous sodium hydroxide, extracting with toluene, washing with water, drying with anhydrous sodium sulfate, filtering, concentrating and vacuum drying to obtain 4.94 g of a crude product of the optically active secondary amine (4g) represented by the following formula:

[Chemical 49]

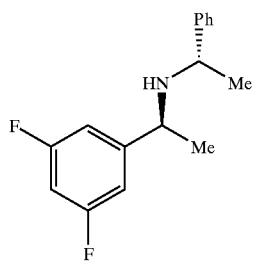

[4g]

Conversion and diastereomer ratio of the crude product were determined by chiral GC and found to be 100% and S-S:R-S-87:13, respectively.

S-S form $^1$H-NMR (TMS, CDCl$_3$): 1.22 (d, 6.8 Hz, 3H), 1.28 (d, 6.8 Hz, 3H), 1.52 (br, 1H), 3.48 (q, 6.8 Hz, 2H), 6.58–6.83 (Ar—H, 3H), 7.12–7.37 (Ar—H, 5H).

R-S form $^1$H-NMR (TMS, CDCl$_3$): 1.31 (d, 6.6 Hz, 3H), 1.35 (d, 6.6 Hz, 3H), 1.52 (br, 1H), 3.73 (q, 6.6 Hz, 1H), 3.76 (q, 6.6 Hz, 1H), 6.58–6.83 (Ar—H, 3H), 7.12–7.37 (Ar—H, 5H).

Example 29

Step 3: Hydrogenolysis 394 mg (1.51 mmol) of the crude product of the optically active secondary amine (4g) produced in Example 28 and 7.8 mg (0.05 wt % as Pd) of 5% palladium/active carbon (water content: 50 wt %) were added to 1.5 ml of methanol, followed by setting the hydrogen pressure to 0.5 MPa and stirring for 21 hours at 60° C. Following completion of the reaction, the reaction liquid was filtered with Celite, concentrated and vacuum dried to obtain a crude product of the optically active 1-(3,5-difluorophenyl)ethylamine (5g) represented by the following formula:

[Chemical 50]

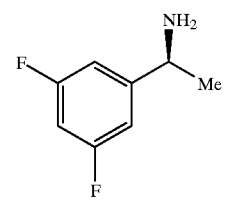

[5g]

Conversion, selectivity at the cleavage position (the previously mentioned a:b) and optical purity of the crude product were determined by chiral GC and found to be 79%, a:b=0:100 and 74% ea, respectively.

$^1$H-NMR (TMS, CDCl$_3$): 1.38 (d, 6.6 Hz, 3H), 2.60 (br, 2H), 4.09 (q, 6.6 Hz, 1H), 6.60–7.00 (Ar—H, 3H).

Example 30

Recrystallization Purification by p-Toluenesulfonic Acid Salt of Optically Active 1-(3,5-Bis-trifluoromethylphenyl)ethylamine (5a)

1.02 g (3.97 mmol, 1 eq) of optically active 1-(3,5-bis-trifluoromethylphenyl)ethylamine (5a, enantiomer ratio/S form:R form=7.4:1) and 0.68 g (3.59 mmol, 0.9 eq) of p-toluenesulfonic acid monohydrate were added to 6.5 ml of toluene, followed by stirring for 30 minutes at 60–70° C., the addition of 6 ml of n-hexane and allowing to cool to room temperature and stand for one day. The precipitated crystals were filtered, washed with a small amount of n-hexane and vacuum dried to obtain 0.20 g of crystals having the structure represented by the formula below and 1.44 g of mother liquor. They were converted to the free bases with 0.5 N aqueous NaOH and analyzed by chiral GC. With this, respective ee were found to be 82.7% ee (major form is the S form) and 74.2% ee (major form is the S form).

[Chemical 51]

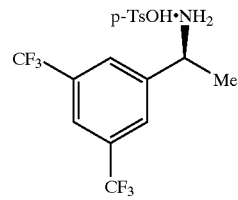

$^1$H-NMR (TMS, DMSO): 1.54 (d, 6.8 Hz, 3H), 2.28 (s, 3H), 4.69 (q, 6.8 Hz, 1H), 7.10 (d, 8.3 Hz, 2H), 7.46 (d, 8.3 Hz, 2H), 8.17 (s, 1H), 8.23 (s, 2H), 8.30 (br, 31).

Example 31

Recrystallization Purification by d-Tartaric Acid Salt of Optically Active 1-(3,5-Bis-trifluoromethylphenyl)ethylamine (5a)

0.94 g (3.64 mmol, 1 eq) of optically active 1-(3,5-bis-trifluoromethylphenyl)ethylamine (5a, enantiomer ratio/S form:R form=7.4:1) and 0.55 g (3.64 mmol, 1 eq) of d-tartaric acid were added to 30 ml of methanol, followed by stirring for 30 minutes under reflux, allowing to cool to room temperature and stand for one half day. The precipitated crystals were filtered, washed with a small amount of methanol and vacuum dried to obtain 1.01 g of crystals having the structure represented by the formula below and 0.48 g of mother liquor. They were converted to the free bases with 0.5 N aqueous NaOH and analyzed by chiral GC. With this, respective ee were found to be 91.4% ee (major form is the S form) and 43.8% ee (major form is the S form).

[Chemical 52]

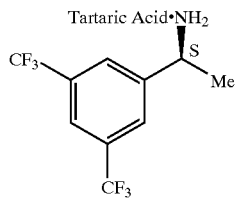

$^1$H-NMR (TMS, DMSO): 1.45 (d, 6.8 Hz, 3H), 3.92 (s, 2H), 4.52 (q, 6.8 Hz, 1H), 6408 (s, 1H), 8.19 (s, 2H).

Example 32

Recrystallization Purification by (S)-Mandelic Acid Salt of Optically Active 1-(3,5-Bis-trifluoromethylphenyl)ethylamine (5a)

0.64 g (2.49 mmol, 1 eq) of optically active 1-(3,5-bis-trifluoromethylphenyl)ethylamine (5a, enantiomer ratio/S form:R form=3.8:1) and 0.17 g (1.12 mmol, 0.45 eq) of (S)-mandelic acid were added to 3 ml of toluene, followed by stirring for 30 minutes under reflux, the addition of 1.5 ml of n-hexane and allowing to cool to room temperature and stand for 2 days in a refrigerator. The precipitated crystals were filtered, washed with a small amount of n-hexane and vacuum dried to obtain 0.53 g of crystals having the structure represented by the formula below and 0.28 g of mother liquor. They were converted to the free bases with 0.5 N aqueous NaOH and analyzed by chiral GC. With this, respective ee were found to be 96.1% ee (major form is the S form) and 4.7% ee (major form is the S form).

[Chemical 53]

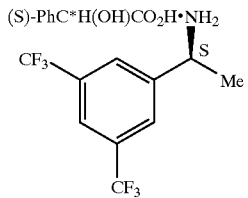

$^1$H-NMR (TMS, DMSO): 1.39 (d, 6.8 Hz, 3H), 4.41 (q, 6.5 Hz, 1H), 4.71 (d, 2.0 Hz, 1H), 7.19 (t, 7.3 Hz, 1H), 7.26 (t, 7.3 Hz, 2H), 7.36 (d, 7.3 Hz, 2H), 8.01 (s, 1H), 8.15 (s, 2H).

Example 33

Recrystallization Purification by (s)-Mandelic Acid Salt of Optically Active 1-(3.5-Bis-trifluoromethylphenyl)ethylamine (5a)

0.80 g (3.10 mmol, 1 eq) of optically active 1-(3,5-bis-trifluoromethylphenyl)ethylamine (5a, enantiomer ratio/S form:R form=8.8:1) and 0.47 g (3.09 mmol, 1 eq) of (S)-mandelic acid were added to 4.5 ml of toluene, followed by stirring for 30 minutes under reflux, the addition of 1.8 ml of n-hexane, allowing to cool to room temperature, adding seed crystals and allowing to stand for 3 hours. The precipitated crystals were filtered, washed with a small amount of a-hexane and vacuum dried to obtain 0.89 g of crystals having the structure represented by the formula below and 0.35 g of mother liquor. They were converted to the free bases with 0.5 N aqueous NaOH and analyzed by chiral GC. With this, respective ee were found to be 90.7% ee (major form is the S form) and 58.1% ee (major form is the S form).

[Chemical 54]

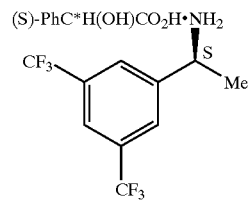

The $^1$H-NMR spectrum was the same as that of Example 32.

Example 34

Recrystallization Purification by (S)-Mandelic Acid Salt of Optically Active 1-(3,5-Bis-trifluoromethylphenyl)ethylamine (5a)

0.89 g of (S)-mandelic acid salt of optically active 1-(3, 5-bis-trifluoromethylphenyl)ethylamine (5a) (5a (S)-mandelate, enantiomer ratio/S form:R form=95.5:4.5) were added to 10 ml of toluene, followed by stirring for 30 minutes at 80° C. and allowing to cool to room temperature and stand for 1 hour. The precipitated crystals were filtered, washed with a small amount of toluene and vacuum dried to obtain 0.71 g of crystals having the structure represented by the formula below and 0.18 g of mother liquor. They were converted to the free bases with 0.5 N aqueous NaOH and analyzed by chiral GC. With this, respective ee were found to be 99.7% ee (major form is the S form) and 82.7% ee (major form is the S form).

[Chemical 55]

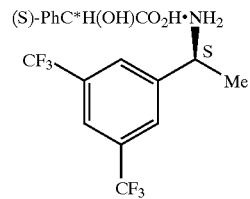

The 1H-NMR spectrum was the same as that of Example 32.

Example 35

Recrystallization Purification by Hydrochloride of Optically Active Secondary Amine (4a)

2.32 g (6.43 mmol) of optically active secondary amine (4a, diastereomer ratio/S-S form:R-S form 7.5:1) were dissolved in 20 ml of methanol, followed by the excess addition of 10% methanol hydrochloride while cooling with ice, stirring for 30 minutes at the same temperature, concentrating and vacuum drying to obtain a crude product of the hydrochloride of 4a at the quantitative yield. 30 ml of a mixed solution of n-hexane-ethanol (50:1) were added to the crude product followed by stirring and washing for 30 minutes at 50° C. and allowing to cool to room temperature and stand overnight. The precipitated crystals were filtered, washed with a small amount of n-hexane and vacuum dried to obtain 1.98 g of crystals having the structure represented by the formula below and 0.58 g of mother liquor. They were converted to the free bases with 0.5 N aqueous NaOH and analyzed by chiral GC. With this, respective de were found to be 82.4% de (major form is the S-S form) and 54.7% de (major form is the S-S form).

[Chemical 56]

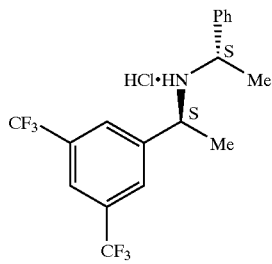

$^1$H-NMR (TMS, DMSO): 1.58 (d, 6.8 Hz, 3H), 1.62 (d, 6.8 Hz, 3H), 3.99 (q, 6.8 Hz, 1H), 4.28 (q, 6.8 Hz, 1H), 7.25–7.48 (m, 5H), 8.13 (s, 3H), 10.22 (br, 1H), 10.53 (br, 1H).

Example 36

Recrystallization Purification by p-Toluenesulfonic Acid Salt of Optically Active Secondary Amine (4a)

3.04 g (8.42 mmol, 1 eq) of optically active secondary amine (4a, diastereomer ratio/S-S form:R-S form=7.5:1) and 1.60 g (8.42 mmol, 1 eq) of p-toluenesulfonic acid monohydrate were added to 42 ml of t-butylmethyl ether, followed by stirring for 40 minutes at 60° C., the addition of 72 ml of n-hexane, allowing to cool to room temperature, adding seed crystals and allowing to stand overnight. The precipitated crystals were filtered, washed with a small amount of n-hexane and vacuum dried to obtain 3.12 g of crystals having the structure represented by the formula below and 1.37 g of mother liquor. They were converted to the free bases with 0.5 N aqueous NaOH and analyzed by chiral GC. With this, respective de were found to be 99.3% de (major form is the S-S form) and 16.6% de (major form is the S-S form).

[Chemical 57]

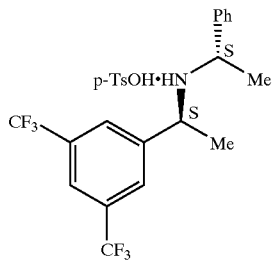

$^1$H-NMR (TMS, DMSO): 1.55 (d, 6.0 Hz, 3H), 1.58 (d, 6.0 Hz, 3H) 2.28 (s, 3H), 4.29 (q, 6.0 Hz, 1H), 4.54 (q, 6.0 Hz, 1H), 7.11 (d, 8.0 Hz, 2H), 7.38 (m, 2H), 7.43 (m, 3H), 7.47 (d, 8.0 Hz, 2H), 8.10 (s, 2H), 8.20 (s, 1H), 9.41 (br, 2H).

Example 37

Recrystallization Purification by (S)-Mandelic Acid Salt of Optically Active Secondary Amine (4a)

0.81 g (2,23 mmol, 1 eq) of optically active secondary amine (4a, diastereomer ratio/S-S form:R-S form=7:1) and 0.34 g (2.23 mmol, 1eq) of (S)-mandelic acid were added to 1 ml of toluene, followed by stirring for 30 minutes at 60° C., the addition of 6 ml of n-hexane and allowing to cool to room temperature and stand overnight. The precipitated crystals were filtered, washed with a small amount of n-hexane and vacuum dried to obtain 0.99 go f crystals having the structure represented by the formula below and 0.12 g of mother liquor. They were converted to the free bases with 0.5 N aqueous NaOH and analyzed by chiral GC. With this, respective de were found to be 77.2% de (major form is the S-S form) and 57.8% de (major form is the S-S form).

[Chemical 58]

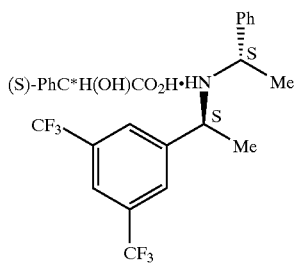

$^1$H-NMR (TMS, DMSO): 1.19 (d, 6.4 Hz, 3H), 1.23 (d, 6.4 Hz, 3H), 3.29 (q, 6.4 Hz, 1H), 3.60 (q, 6.4 Hz, 1H), 4.99 (s, 1H), 7.07–7.46 (m, 10H), 7.92 (s, 2H), 7.94 (s, 1H).

Example 38

Conversion of Purifted Optically Active Secondary Amine (4a)·p-Toluenesulfonate to Optically Active 1-(3,5-Bis-trifluoromethylphenyl)ethylamine (5a)

13.3 g (24.95 mmol, 1 eq) of the p-toluenesulfonate of optically active secondary amine (4a) purified with reference to Example 36 (4a.p-toluenesulfonate, 99.6% de, major form: S-S form) and 100 ml (50 mmol, 2 eq) of 0.5 N aqueous NaOH were added to 50 ml of toluene, followed by stirring for 30 minutes at room temperature, separating statically, extracting the recovered aqueous layer with toluene, washing the combined recovered organic layers with saturated brine, drying with an hydrous sodium sulfate, filtering, concentrating and vacuum drying to obtain an optically active secondary amine (4a) having the structure indicated below at the quantitative yield.

[Chemical 59]

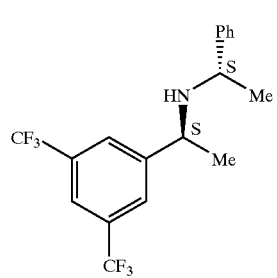

[4a]

The resulting 4a was dissolved in 26 ml of methanol, followed by the addition of 0.45 g (0.125 wt %) of 5% palladium/active carbon (water content: 50 wt %), setting the hydrogen pressure to 0.2 MPa and stirring for 22 hours at 60° C. Following completion of the reaction, the reaction liquid was filtered with Celite, concentrated and vacuum dried to obtain a crude product of optically active 1-(3, 5-bis-trifluoromethylphenyl)ethylamine (5a) having the structure indicated below at the quantitative yield. The crude product was purified by simple distillation (96–97° C./31 mmHg) to obtain 5.41 g of a highly pure product (total yield for the two steps: 84%). GC purity and ee were 99.4% and 99.4% ee, respectively.

[Chemical 60]

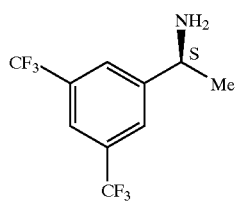

[5a]

Example 39

Recrystallization Purification by Phthalate of Optically Active Secondary Amine (4c)

1.00 g (3.41 mmol, 1 eq) of optically active secondary amine (4c, diastereomer ratio/S-S form: R-S form 86:14) and 0.56 g (3.37 mmol, 1 eq) of phthalic acid were added to 3.5 ml of i-propanol, followed by stirring for 30 minutes at 60–70° C., the addition of 5 ml of n-hexane and allowing to cool to room temperature and stand for 63 hours. The precipitated crystals were filtered, washed with a small amount of n-hexane and vacuum dried to obtain 1.36 g of crystals having the structure represented by the formula below and 0.20 g of mother liquor. They were converted to the free bases with 0.5 N aqueous NaOH and analyzed by chiral GC. With this, respective de were found to be 95.8% de (major form is the S-S form) and 43.9% de (major form is the R-S form).

[Chemical 61]

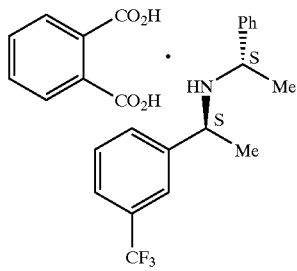

$^1$H-NMR (TMS, CDCl$_3$): 1.80 (d, 7.2 Hz, 3H), 1.84 (d, 7.2 Hz, 3H), 4.01 (q, 7.2 Hz, 1H), 4.15 (q, 7.2 Hz, 1H), 7.35–7.88 (m, 11H), 8.48–8.59 (m, 2H), 10.60 (br, 3H).

Example 40

Recrystallization Purification by Hydrobromate of Optically Active Secondary Amine (4c)

1.00 g (3.41 mmol, 1 eq) of optically active secondary amine (4c, diastereomer ratio/S-S form:R-S form=84:16) and 0.4 ml (3.44 mmol, 1 eq) of 47% hydrobromic acid were added to 3 ml of methanol, followed by stirring for 30 minutes at 80° C. and concentrating under reduced pressure. 6 ml of i-propanol and 6 ml of n-heptane were added to the residue followed by stirring for 67 hours at room temperature. The precipitated crystals were filtered, washed with a small amount of n-heptane and vacuum dried to obtain 1.03 g of crystals having the structure represented by the formula below and 0.24 g of mother liquor. They were converted to the free bases with 0.5 N aqueous NaOH and analyzed by chiral GC. With this, respective de were found E to be 80.6% de (major form is the S-S form) and 2.9% de (major form is the S-S form). Moreover, 1.03 g of the resulting crystals were added to 10 ml of i-propanol and dissolved while heating followed by the addition of 3 ml of n-heptane and stirring for 16 hours at room temperature. The precipitated crystals were filtered, washed with a small amount of n-heptane and vacuum dried to obtain 0.78 g of crystals having the structure represented by the formula below and 0.22 g of mother liquor. They were converted to the free bases with 0.5 N aqueous NaOH and analyzed by chiral GC. With this, respective de were found to be 99.3%t de (major form is the S-S form) and 10.3% de (major form is the S-S form)

[Chemical 62]

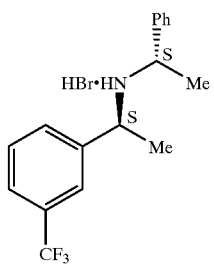

$^1$H-NMR (TMS, CDCl$_3$): 2.00 (d, 6.8 Hz, 3H), 2.04 (d, 6.8 Hz, 3H), 3.89 (m, 1H), 4.04 (m, 1H), 7.34–8.22 (m, 9H), 10.20 (br, 2H).

Example 41

Recrystallization Purification by Phthalate of Optically Active Secondary Amine (4d)

1.00 g (3.41 mmol, 1 eq) of optically active secondary amine (4d, diastereomer ratio/S-S form: R-S form=84:16) and 0.56 g (3.37 mmol, 1 eq) of phthalic acid were added to 3.5 ml of i-propanol, followed by stirring for 30 minutes at 60–70° C., the addition of 5 ml of n-hexane and allowing to cool to room temperature and stand for 23 hours. The precipitated crystals were filtered, washed with a small amount of n-hexane and vacuum dried to obtain 1.24 g of crystals having the structure represented by the formula below and 0.30 g of mother liquor. They were converted to the free bases with 0.5 N aqueous NaOH and analyzed by chiral GC. With this, respective de were found to be 93.8% de (major form is the S-S form) and 51.5% de (major form is the R-S form). Moreover, 1.20 g of the resulting crystals were added to 3 ml of i-propanol, followed by stirring for 30 minutes at 60–70° C., the addition of 2 ml of n-hexane and allowing to cool to room temperature and stand for 2 hours. The precipitated crystals were filtered, washed with a small amount of n-hexane and vacuum dried to obtain 1.08 g of crystals having the structure represented by the formula below and 0.12 g of mother liquor. They were converted to the free bases with 0.5 N aqueous NaOH and analyzed by chiral GC. With this, respective de were found to be 99.0% de (major form is the S-S form) and 26.1% de (major form is the S-S form).

[Chemical 63]

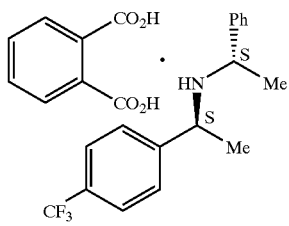

$^1$H-NMR (TMS, CDCl$_3$): 1.80 (d, 6.8 Hz, 6H), 4.04 (q, 6.8 Hz, 1H), 4.13 (q, 6.8 Hz, 1H), 7.35–7.73 (m, 11H), 8.45–8.55 (m, 2H), 10.60 (br, 3H).

Example 42

Recrystallization Purification by Benzenesulfonate of Optically Active Secondary Amine (4d)

1.00 g (3.41 mmol, 1 eq) of optically active secondary amine (4d, diastereomer ratio/S-S form:R-S form=84:16) and 0.60 g (3.41 mmol, 1 eq) of benzenesulfonic acid monohydrate were added to 3–5 ml of i-propanol, followed by stirring for 30 minutes at 60–70° C., the addition of 5 ml of n-hexane and allowing to cool to room temperature and stand for 1 day. The precipitated crystals were filtered, washed with a small amount of n-hexane and vacuum dried to obtain 1.32 g of crystals having the structure represented by the formula below and 0.20 g of mother liquor. They were converted to the free bases with 0.5 N aqueous NaOH and analyzed by chiral GC. With this, respective de were found to be 80.9% de (major form is the S-S form) and 11.7% de (major form is the R-S form). Moreover, 1.32 g of the resulting crystals were added to 3–9 ml of i-propanol, followed by stirring for 30 minutes at 60–70° C., the addition of 2 ml of n-hexane and allowing to cool to room temperature and stand overnight. The precipitated crystals were filtered, washed with a small amount of n-hexane and vacuum dried to obtain 1.05 g of crystals having the structure represented by the formula below and 0.21 g of mother liquor. They were converted to the free bases with 0.5 N aqueous NaOH and analyzed by chiral GC. With this, respective de were found to be 98.6% de (major form is the S-S form) and 17.6% de (major form is the R-S form).

[Chemical 64]

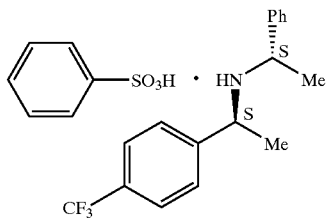

$^1$H-NMR (TMS, CDCl$_3$): 1.84 (d, 5.6 Hz, 6H), 3.84 (q, 5.6 Hz, 1H), 3.95 (q, 5.6 Hz, 1H), 7.20–7.60 (m, 12H), 8.03–8.17 (m, 2H), 9.73 (br, 2H).

Example 43

Conversion of Purified Optically Active Secondary Amine (4c)·Phthalate to Optically Active 1-(3-Trifluoromethylphenyl)ethylamine (5c)

1.00 g (2.18 mmol, 1 eq) of the phthalate of optically active secondary amine (4c) purified in Example 39 (4c.phthalate, 95.8% de, major form: S-S) and 17.4 ml (8.72 mmol, 4 eq) of 0.5 N aqueous NaOH were added to 10 ml of toluene, followed by stirring for 30 minutes at room temperature, separating statically, extracting the recovered aqueous layer with 5 ml of toluene, washing the combined recovered organic layers with saturated brine, drying with anhydrous sodium sulfate, filtering, concentrating and vacuum drying to obtain optically active secondary amine (4c) having the structure indicated below at the quantitative yield.

[Chemical 65]

[4c]

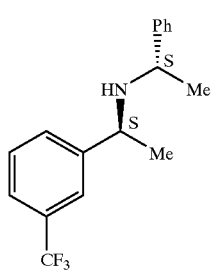

The resulting 4c was dissolved in 2.2 ml of methanol followed by the addition of 12.8 mg (0.05 wt %) of St palladium/active carbon (water content: 50 wt %), setting the hydrogen pressure to 0.5 MPa and stirring for 24 hours at 60° C. Following completion of the reaction, the reaction liquid was filtered with Celite, concentrated and vacuum dried to obtain a crude product of optically active 1-(3-trifluoromethylphenyl)ethylamine (5c) having the structure indicated below. Conversion and optical purity of the crude product were determined by chiral GC and found to be 96% and 95.6% ee, respectively.

[Chemical 66]

[5c]

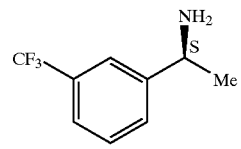

Example 44

Conversion of Purified Optically Active Secondary Amine (4d)·Phthalate to Optically Active 1-(4-Trifluoromethylphenyl)ethylamine (5d)

1.00 g (2.18 mmol, 1 eq) of the phthalic acid salt of optically active secondary amine (4d) purified in Example 41 (4d.phthalate, 99.0% de, major form; S-S form) and 17.4 ml (8.72 mmol, 4 eq) of 0.5 N aqueous NaOH were added to 10 ml of toluene, followed by stirring for 30 minutes at room temperature, separating statically, extracting the recovered aqueous layer with 5 ml of toluene, washing the combined recovered organic layers with saturated brine, drying with anhydrous sodium sulfate, filtering, concentrating and vacuum drying to obtain optically active secondary amine (4d) having the structure indicated below at the quantitative yield.

[Chemical 67]

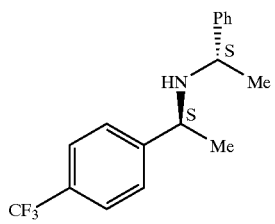

[4d]

The resulting 4d was dissolved in 2.2 ml of methanol, followed by the addition of 12.8 mg (0.05 wt %) of 5% palladium/active carbon (water content: 50 wt %), setting the hydrogen pressure to 0.5 MPa and stirring for 24 hours at 60° C. Following completion of the reaction, the reaction liquid was filtered with Celite, concentrated and vacuum dried to obtain a crude product of optically active 1-(4-trifluoromethylphenyl)ethylamine (5d) having the structure indicated below. Conversion and optical purity of the crude product were determined by chiral GC and found to be 97% and 98.9% ee, respectively.

[Chemical 68]

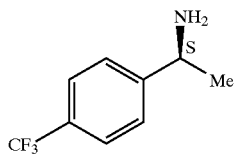

[5d]

Example 45

Conversion of Purified Optically Active Secondary Amine (4d)˙Benzenesulfonate to Optically Active 1-(4-Trifluoromethylphenyl)ethylamine (5d)

1.00 g (2.22 mmol, 1 eq) of the benzenesulfonic acid salt of optically active secondary amine (4d) purified in Example 42 (4d.benzenesulfonate, 98.6% de, major form: S-S form) and 13.3 ml (6.66 mmol, 3 eq) of 0.5 N aqueous NaOH were added to 10 ml of toluene, followed by stirring for 30 minutes at room temperature, separating statically, extracting the recovered aqueous layer with 5 ml of toluene, washing the combined recovered organic layers with saturated brine, drying with anhydrous sodium sulfate, filtering, concentrating and vacuum drying to obtain optically active secondary amine (4d) having the structure indicated below at the quantitative yield.

[Chemical 69]

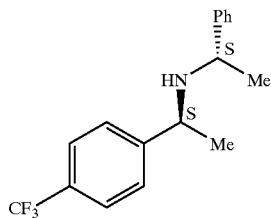

[4d]

The resulting 4d was dissolved in 2.2 ml of methanol followed by the addition of 13.0 mg (0.05 wt %) of 5% palladium/active carbon (water content: 50 wt %), setting the hydrogen pressure to 0.5 MPa and stirring for 24 hours at 60° C. Following completion of the reaction, the reaction liquid was filtered with Celite, concentrated and vacuum dried to obtain a crude product of optically active 1-(4-trifluoromethylphenyl)ethylamine (5d) having the structure indicated below. Conversion and optical purity of the crude product were determined by chiral GC and found to be 97% and 98.4% ee, respectively.

[Chemical 70]

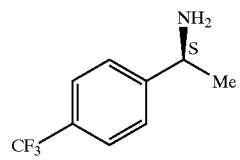

[5d]

Example 46

Recrystallization Purification by Hydrochloric Acid Salt of Optically Active Secondary Amine (4f)

1.00 g (4.11 mmol, 1 eq) of optically active secondary amine (4f, diastereomer ratio/S-S form:R-S form=93:7) and 0.4 ml (4.87 mmol, 1.18 eq) of 37% hydrochloric acid were added to 3 ml of methanol, followed by stirring for 30 minutes at 80° C. and concentrating under reduced pressure. 5 ml of i-propanol and 3 ml of n-heptane were added to the residue and dissolved while heating followed by stirring for 18 hours while cooling to room temperature. The precipitated crystals were filtered, washed with a small amount of n:-heptane and vacuum dried to obtain 0.85 g of crystals having the structure represented by the formula below and 0.26 g of mother liquor. They were converted to the free bases with 0.5 N aqueous NaOH and analyzed by chiral GC. With this, respective de were found to be 95.8% de (major form is the S-S form) and 47.6% ee (major form is the S-S form).

[Chemical 71]

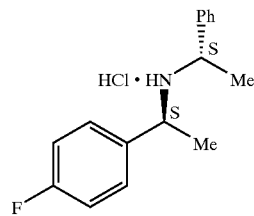

$^1$H-NMR (TMS, CDCl$_3$): 1.91 (d, 6.6 Hz, 6H), 3.75–4.00 (m, 2H), 7.00–7.80 (Ar—H, 9H), 10.52 (br, 2H).

Example 47

Recrystallization Purification by Hydrobromic Acid Salt of Optically Active Secondary Amine (4f)

1.01 g (4.14 mmol, 1 eq) of optically active secondary amine (4f, diastereomer ratio/S-S form: R-S form=93:7) and 0.5 ml (4.30 mmol, 1.04 eq) of 47% hydrobromic acid were added to 3 ml of methanol, followed by stirring for 30 minutes at 80° C. and concentrating under reduced pressure. 8 ml of i-propanol and 3 ml of n-heptane were added to the residue and dissolved while heating followed by stirring for 66 hours while cooling to room temperature. The precipitated crystals were filtered, washed with a small amount of n-heptane and vacuum dried to obtain 0.91 g of crystals having the structure represented by the formula below and 0.28 g of mother liquor. They were converted to the free bases with 0.5 N aqueous NaOH and analyzed by chiral GC. With this, respective de were found to be 98.4% de (major form is the S-S form) and 37.0% de (major form is the S-S form).

[Chemical 72]

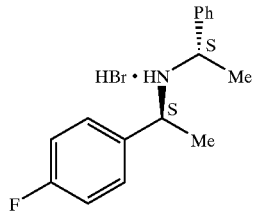

$^1$H-NMR (TMS, CDCl$_3$): 1.98 (d, 6.8 Hz, 6H), 3.80–4.10 (m, 2H), 7.00–7.80 (Ar—H, 9H), 10.01 (br, 2H).

Example 48

Recrystallization Purification by Phthalic Acid Salt of Optically Active Secondary Amine (4e)

1.00 g (4.12 mmol, 1 eq) of optically active secondary amine (4e, diastereomer ratio/S-S form:R-S form=86:14) and 0.68 g (4.09 mmol, 0.99 eq) of phthalic acid were added to a mixed solution of 3 ml of i-propanol and 3 ml of n-heptane, followed by stirring for 30 minutes at 80° C. and concentrating under reduced pressure. 17.5 ml of i-propanol were added to the residue and dissolved while heating, followed by stirring for 18 hours while cooling to room temperature. The precipitated crystals were filtered, washed with a small amount of n-heptane and vacuum dried to obtain 1.32 g of crystals having the structure represented by the formula below and 0.47 g of mother liquor. They were converted to the free bases with 0.5 N aqueous NaOH and analyzed by chiral GC. With this, respective de were found to be 99.2% de (major form is the S-S form) and 46.0% de (major form is the R-S form).

[Chemical 73]

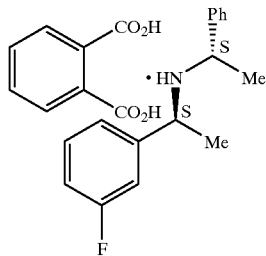

$^1$H-NMR (TMS, CDCl$_3$): 1.78 (d, 7.0 Hz, 3H), 1.80 (d, 7.0 Hz, 3H), 4.05 (m, 2H), 7.04–7.70 (Ar—H, 11H), 8–45–8.58 (Ar—H, 2H), 10.48 (br, 3H).

Example 49

Recrystallization Purification by Phthalic Acid Salt of Optically Active Secondary Amine (49)

1.01 g (3.85 mmol, 1 eq) of optically active secondary amine (4g, diastereomer ratio/S-S form:R-S form=87:13) and 0.64 g (3.83 mmol, 0.99 eq) of phthalic acid were added to a mixed solution of 5 ml of i-propanol and 6 ml of methanol and dissolved while heating, followed by stirring for 19 hours while cooling to room temperature. The precipitated crystals were filtered, washed with a small amount of n-heptane and vacuum dried to obtain 1.05 g of crystals having the structure represented by the formula below and 0.54 g of mother liquor. They were converted to the free bases with 0.5 N aqueous NaOH and analyzed by chiral GC. With this, respective de were found to be 99.6% de (major form is the S-S form) and 9.1% de (major form is the R-S form).

[Chemical 74]

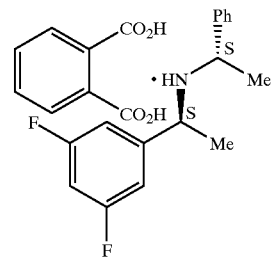

$^1$H-NMR (TMS, CDCl$_3$): 1.77 (d, 6.6 Hz, 3H), 1.81 (d, 6.6 Hz, 3H), 4.03 (q, 6.6 Hz, 1H), 4.10 (q, 6.6 Hz, 1H), 6.75–7.70 (Ar—H, 10H), 8.45–8.58 (Ar—H, 2H), 10.79 (br, 3H).

Example 50

Conversion of Purified optically Active Secondary Amine (4f)-Hydrochloride to Optically Active 1-(4-Fluorophenyl)ethylamine (5f)

309 mg (1.10 mmol, 1 eq) of the hydrochloric acid salt of optically active secondary amine (4f) purified in Example 46 (4f.hydrochloride, 95.8% de, major form: S-S form) were dissolved in 1.5 ml of methanol followed by the addition of 5.6 mg (0.05 wt % as Pd) of 5% palladium/active carbon (water content: 50 wt %), setting the hydrogen pressure to 0.5 MPa and stirring for 15 hours at 60° C. Following completion of the reaction, the reaction liquid was filtered with celite, concentrated and vacuum dried to obtain the hydrochloric acid salt of optically active 1-(4-fluorophenyl)ethylamine (5f) (5f.hydrochloride). 10 ml of t-butylmethyl ether and 10 ml of 0.5 N aqueous NaOH were added to this hydrochloric acid salt, followed by stirring for 30 minutes at room temperature, separating statically, extracting the recovered aqueous layer with 5 ml of t-butylmethyl ether, washing the combined recovered organic layers with saturated brine, drying with anhydrous sodium sulfate, filtering, concentrating and vacuum drying to obtain a crude product of optically active 1-(4-fluorophenyl)ethylamine (5f) having the structure indicated below. Conversion and optical purity of the crude product were determined by chiral GC and found to be >99% and 95.6% ee, respectively.

[Chemical 75] [5f]

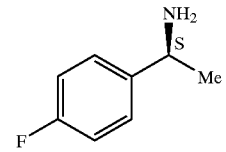

$^1$H-NMR (TMS, CDCl$_3$): 1.39 (d, 6.6 Hz, 3H), 2.10 (br, 2H), 4.11 (q, 6.6 Hz, 1H), 7.12–7.38 (Ar—H, 4H).

Example 51

Conversion of Purified Optically Active Secondary Amine (4e)˙Phthalate to Optically Active 1-(3-Fluorophenyl)ethylamine (5e)

615 mg (1.50 mmol, 1 eq) of the phthalic acid salt of optically active secondary amine (4e) purified in Example 48 (4e.phthalate, 99.2% de, major form: S-S form) were dissolved in 4.0 ml of methanol followed by the addition of 7.3 mg (0.03 wt % as Pd) of 5% palladium/active carbon (water content: 50%), setting the hydrogen pressure to 0.5 MPa and stirring for 14 hours at 60° C. Following completion of the reaction, the reaction liquid was filtered with Celite, concentrated and vacuum dried to obtain the phthalic acid salt of optically active 1-(3-fluorophenyl)ethylamine (5e) (5e.phthalate). 10 ml of t-butylmethyl ether and 10 ml of 0.5 N aqueous NaOH were added to this phthalic acid salt, followed by stirring for 30 minutes at room temperature, separating statically, extracting the recovered aqueous layer with 5 ml of t-butylmethyl ether, washing the combined recovered organic layers with saturated brine, drying with anhydrous sodium sulfate, filtering, concentrating and vacuum drying to obtain a crude product of optically active 1-(3-fluorophenyl)ethylamine (5e) having the structure indicated below. Conversion and optical purity of the crude product were determined by chiral GC and found to be 99.5% and 99.1% ee, respectively.

[Chemical 76]

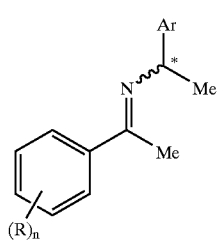

[5e]

$^1$-NMR (TMS, CDCl$_3$): 1.40 (d, 6.6 Hz, 3H), 2.80 (br, 2H), 4.10 (q, 6.6 Hz, 1H), 6.86–7.42 (Ar—H, 4H).

What is claimed is:

1. A process for producing an optically active 1-(fluoro- or trifluoromethyl-substituted phenyl)ethylamine represented by formula 5:

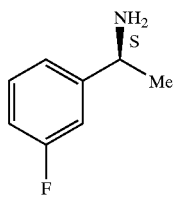

[5]

wherein R represents a fluorine atom or trifluoromethyl group, n represents 1 to 5 and R takes an arbitrary substitution position, except for the ortho position when R is a fluorine atom and n is 1, and the asterisk represents a chiral carbon, comprising:

asymmetrically reducing an optically active imine represented by formula 3:

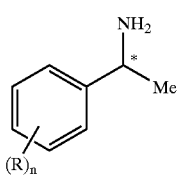

[3]

wherein R represents a fluorine atom or trifluoromethyl group, n represents 1 to 5 and R takes an arbitary substitution position, except for the ortho position when R is a fluorine atom and n is 1, Ar represents a phenyl group or 1- or 2-naphthyl group, and the asterisk represents a chiral carbon using a hydride reducing agent, converting to an optically active secondary amine represented by formula 4:

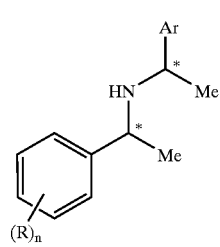

[4]

wherein R represents a fluorine atom or trifluoromethyl group, n represents 1 to 5 and R takes an arbitrary substitution position, except for the ortho position when R is a fluorine atom and n is 1, Ar represents a phenyl group or 1- or 2-naphthyl group, and the asterisks represent chiral carbons), and subjecting the secondary amine, its salt of an inorganic acid or its salt of an organic acid to hydrogenolysis.

2. The process according to claim 1, wherein the hydride reducing agent is sodium borohydride.

3. The process according to claim 1, wherein the inorganic acid or organic acid comprises hydrochloric acid, hydrobromic acid, phthalic acid, benzenesulfonic acid, p-toluenesulfonic acid or optically active mandelic acid.

4. A process for producing an optically active 1-(fluoro- or trifluoromethyl-substituted phenyl)ethylamine represented by the formula 5:

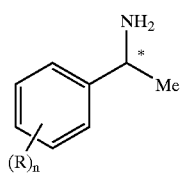

[5]

wherein R represents a fluorine atom or trifluoromethyl group, n represents 1 to 5, and R takes an arbitrary substitution position, except for the ortho position when R is a fluorine atom and n is 1, and the asterisk represents a chiral carbon, comprising:

asymmetrically reducing an optically active imine represented by the formula 3:

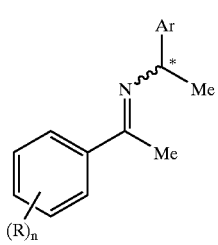

[3]

wherein R represents a fluorine atom or trifluoromethyl group, n represents 1 to 5 and R takes an arbitary substitution position, except for the ortho position when R is a fluorine atom and n is 1, Ar represents a phenyl group or 1- or 2-naphthyl group, and the asterisk represents a chiral carbon, using a hydride reducing agent, converting to an optically active secondary amine represented by the formula 4:

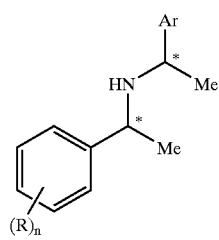

[4]

wherein R represents a fluorine atom or trifluoromethyl group, n represents 1 to 5 and R takes an arbitrary substitution position, except for the ortho position when R is a fluorine atom and n is 1, Ar represents a phenyl group or 1- or 2-naphthyl group, and the asterisks represent chiral carbons, and subjecting the secondary amine, its salt of an inorganic acid or its salt of an organic acid to hydrogenolysis, wherein hydrogenolysis is carried out while heating at 40° C. or higher using a group VIII metal catalyst at 0.5 wt % or less when converted as metal in a hydrogen atmosphere of 2 MPa or lower.

5. The process according to claim 1, wherein the optically active imine represented by formula 3 is an optically active imine obtained by dehydration and condensation under acidic conditions of a fluoro- or trifluoromethyl-substituted phenylmethyl ketone represented by formula 1:

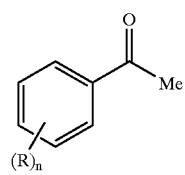

[1]

wherein R represents a fluorine atom or trifluoromethyl group, n represents 1 to 5, and it R takes an arbitrary substitution position, except for the ortho position when R is a fluorine atom and n is 1, and an optically active primary amine represented by formula 2:

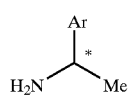

[2]

wherein Ar represents a phenyl group or 1- or 2-naphthyl group, and the asterisk represents a chiral carbon.

6. The process according to claim 1, wherein stereochemistry of the compound represented by formula 3, 4 or 5 is R form or S form.

7. The process according to claim 5, wherein stereochemistry of the compound represented by formula 2 is R form or S form.

8. The process according to claim 1, wherein the optically active secondary amine represented by formula 4:

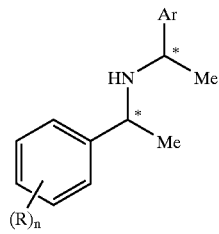

[4]

wherein R represents a fluorine atom or trifluoromethyl group, n represents 1 to 5 and R takes an arbitrary substitution position, except for the ortho position when R is a fluorine atom and n is 1, Ar represents a phenyl group or 1- or 2-naphthyl group, and the asterisks represent chiral carbons, is converted to the salt of the inorganic acid or organic acid, followed by purification by recrystallization.

9. The process according to claim 8, wherein the inorganic acid or organic acid comprises hydrochloric acid, hydrobromic acid, phthalic acid, benzenesulfonic acid, p-toluenesulfonic acid or optically active mandelic acid.

10. The process according to claim 1, wherein the optically active ethylamine represented by the formula 5 is an optically active 1-(3,5-bis-trifluoromethylphenyl) ethylamine represented by formula 6:

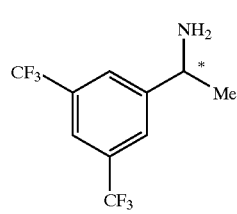

[6]

where the asterisk represents a chiral carbon, wherein the optically active imine represented by the formula 3 is an optically active imine represented by the following formula:

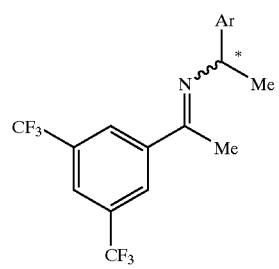

where Ar represents a phenyl group or 1- or 2-naphthyl group, and the asterisk represents a chiral carbon, and wherein the optically active secondary amine represented by the formula 4 is an optically active secondary amine represented by the following formula:

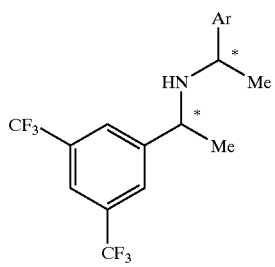

where Ar represents a phenyl group or 1- or 2-naphthyl group, and the asterisks represent chiral carbons.

11. The process according to claim 10, wherein the optically active 1-(3,5-bis-trifluoromethylphenyl) ethylamine represented by the formula 6 is converted to a salt of an inorganic acid or organic acid, followed by purification by recrystallization.

12. The process according to claim 11, wherein the organic acid comprises p-toluenesulfonic acid, optically active mandelic acid or optically active tartaric acid.

13. The process according to claim 8, wherein stereochemistry of the compound represented by formula 4 is R form or S form.

14. The process according to claim 11, wherein stereochemistry of the compound represented by formula 6 is R form.

15. The process according to claim 4, wherein hydrogenolysis is carried out while heating at 55° C. or higher.

16. The process according to claim 1, wherein Ar of formulas 3 and 4 represents a phenyl group or 2-naphthyl group.

17. The process according to claim 1, wherein R of formulas 3, 4 and 5 represents a fluorine atom.

18. A process for producing an optically active 1-(trifluoromethyl-substituted phenyl)ethylamine represented by formula 5:

[5]

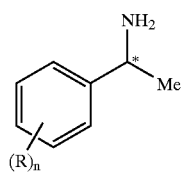

wherein R represents a trifluoromethyl group and takes an arbitrary substitution position, n represents 1 to 5, and the asterisk represents a chiral carbon, comprising:

asymmetrically reducing an optically active imine represented by formula 3:

[3]

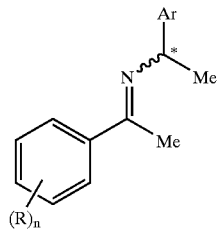

wherein R represents a trifluoromethyl group and takes an arbitrary substitution position, n represents 1 to 5, Ar represents a phenyl group or 1- or 2-naphthyl group, and the asterisk represents a chiral carbon, using a hydride reducing agent, converting to an optically active secondary amine represented by formula 4:

[4]

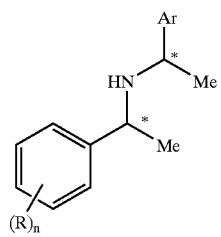

wherein R represents a trifluoromethyl group and takes an arbitrary substitution position, n represents 1 to 5, Ar represents a phenyl group or 1- or 2-naphthyl group, and the asterisks represent chiral carbons, and subjecting the secondary amine, its salt of an inorganic acid or its salt of an organic acid to hydrogenolysis.

19. The process according to claim 4, wherein R in formulas 3, 4 and 5 represents a trifluoromethyl group.

20. The process according to claim 4, wherein R in formulas 3, 4 and 5 represents a fluorine atom.

21. The process according to claim 4, wherein the hydride reducing agent is sodium borohydride.

22. The process according to claim 18, wherein the hydride reducing agent is sodium borohydride.

23. The process according to claim 4, wherein the inorganic acid or organic acid comprises hydrochloric acid, hydrobromic acid, phthalic acid, benzenesulfonic acid, p-toluenesulfonic acid or optically active mandelic acid.

24. The process according to claim 18, wherein the inorganic acid or organic acid comprises hydrochloric acid, hydrobromic acid, phthalic acid, benzenesulfonic acid, p-toluenesulfonic acid or optically active mandelic acid.

25. The process according to claim 4, wherein the optically active imine represented by formula 3 is obtained by dehydration and condensation under acidic conditions of a fluoro- or trifluoromethyl-substituted phenylmethyl ketone represented by formula 1:

[1]

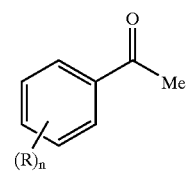

wherein R represents a fluorine atom or trifluoromethyl group and takes an arbitrary substitution position, except R is not in the ortho position when R is a fluorine atom and n is 1, n represents 1 to 5, and an optically active primary amine represented by formula 2:

[2]

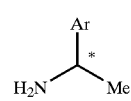

wherein Ar represents a phenyl group or 1- or 2-naphthyl group, and the asterisk represents a chiral carbon.

26. The process according to claim 18, wherein the optically active imine represented by formula 3 is obtained by dehydration and condensation under acidic conditions of a trifluoromethyl-substituted phenylmethyl ketone represented by formula 1:

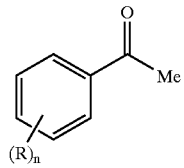

[1]

wherein R represents a trifluoromethyl group and takes an arbitrary substitution position, n represents 1 to 5, and an optically active primary amine represented by formula 2:

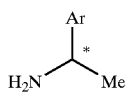

[2]

wherein Ar represents a phenyl group or 1- or 2-naphthyl group, and the asterisk represents a chiral carbon.

27. The process according to claim 4, wherein the stereochemistry of the compound represented by formula 3, 4 or 5 is R form or S form.

28. The process according to claim 18, wherein the stereochemistry of the compound represented by formula 3, 4 or 5 is R form.

29. The process according to claim 4, wherein Ar in formulas 3 and 4 represents a phenyl group or a 2-naphthyl group.

30. The process according to claim 18, wherein Ar in formulas 3 and 4 represents a phenyl group or 2-naphthyl group.

31. The process according to claim 1, wherein the hydrogenolysis is carried out at a temperature of at least 40° C.

32. The process according to claim 1, wherein the hydrogenolysis is carried out at a temperature of at least 40° C. in a hydrogen atmosphere of 2 MPa or lower.

33. The process according to claim 11, wherein stereochemistry of the compound represented by formula 6 is S form.

34. The process according to claim 18, wherein the stereochemistry of the compound represented by formula 3, 4 or 5 is S form.

* * * * *